(12) United States Patent
Fütterer et al.

(10) Patent No.: US 7,524,800 B2
(45) Date of Patent: Apr. 28, 2009

(54) MONO-, DI- AND POLYOL PHOSPHATE ESTERS IN PERSONAL CARE FORMULATIONS

(75) Inventors: Tobias Johannes Fütterer, Singapore (SG); Lawrence Alan Hough, Philadelphia, PA (US); Robert Lee Reierson, Princeton Junction, NJ (US)

(73) Assignee: Rhodia Inc., Cranbury, NJ (US)

( * ) Notice: Subject to any disclaimer, the term of this patent is extended or adjusted under 35 U.S.C. 154(b) by 0 days.

(21) Appl. No.: 12/137,589

(22) Filed: Jun. 12, 2008

(65) Prior Publication Data

US 2008/0312341 A1    Dec. 18, 2008

Related U.S. Application Data

(60) Provisional application No. 60/943,487, filed on Jun. 12, 2007.

(51) Int. Cl.
*C11D 1/72* (2006.01)
*C11D 7/36* (2006.01)
*C11D 3/37* (2006.01)

(52) U.S. Cl. .............. 510/136; 510/130; 510/131; 510/150; 510/228; 510/236; 510/288; 510/319; 510/347; 510/390; 510/423; 510/431; 510/436; 510/467

(58) Field of Classification Search ........... 510/130, 510/131, 136, 150, 228, 236, 288, 319, 347, 510/390, 423, 431, 436, 467
See application file for complete search history.

(56) References Cited

U.S. PATENT DOCUMENTS

| | | | |
|---|---|---|---|
| 2,438,091 A | 3/1948 | Lynch | |
| 2,524,218 A | 10/1950 | Bersworth | |
| 2,528,378 A | 10/1950 | Mannheimer | |
| 2,530,147 A | 11/1950 | Bersworth | |
| 2,658,072 A | 11/1953 | Kosmin | |
| 2,826,551 A | 3/1958 | Geen | |
| 2,874,074 A | 2/1959 | Johnson | |
| 2,946,725 A | 7/1960 | Norris et al. | |
| 3,033,704 A | 5/1962 | Sherrill et al. | |
| 3,070,510 A | 12/1962 | Cooley et al. | |
| 3,244,724 A | 4/1966 | Guttmann | |
| 3,308,067 A | 3/1967 | Diehl | |
| 3,332,880 A | 7/1967 | Kessler et al. | |
| 3,538,230 A | 11/1970 | Pader et al. | |
| 3,553,139 A | 1/1971 | McCarty | |
| 3,598,865 A | 8/1971 | Lew | |
| 3,599,716 A | 8/1971 | Thompson | |
| 3,678,154 A | 7/1972 | Widder et al. | |
| 3,681,241 A | 8/1972 | Rudy | |
| 3,717,630 A | 2/1973 | Booth | |
| 3,723,322 A | 3/1973 | Diehl | |
| 3,793,209 A | 2/1974 | Thompson | |
| 3,850,831 A * | 11/1974 | Hellsten et al. | ............. 510/371 |
| 3,862,307 A | 1/1975 | Di Giulio | |
| 3,869,412 A * | 3/1975 | Waag | ............. 510/467 |
| 3,893,929 A | 7/1975 | Basadur | |
| 3,912,681 A | 10/1975 | Dickson | |
| 3,939,911 A | 2/1976 | Maddox, Jr. et al. | |
| 3,948,838 A | 4/1976 | Hinton, Jr. et al. | |
| 3,956,198 A | 5/1976 | Bauer | |
| 3,959,230 A | 5/1976 | Hays | |
| 3,959,458 A | 5/1976 | Agricola et al. | |
| 3,964,500 A | 6/1976 | Drakoff | |
| 3,976,586 A | 8/1976 | Chakrabarti | |
| 4,001,133 A | 1/1977 | Sorgenfrei et al. | |
| 4,008,165 A | 2/1977 | Maddox, Jr. et al. | |
| 4,017,410 A | 4/1977 | Sorgenfrei et al. | |
| 4,038,027 A | 7/1977 | Kearney | |
| 4,049,558 A | 9/1977 | Rasmussen | |
| 4,051,234 A | 9/1977 | Gieske et al. | |
| 4,101,457 A | 7/1978 | Place et al. | |
| 4,116,984 A | 9/1978 | Prinzbach et al. | |
| 4,127,489 A | 11/1978 | Pracht et al. | |
| 4,144,226 A | 3/1979 | Crutchfield et al. | |
| 4,146,495 A | 3/1979 | Crutchfield et al. | |
| 4,152,416 A | 5/1979 | Spitzer et al. | |
| 4,152,421 A | 5/1979 | Tsutsumi et al. | |
| 4,206,215 A | 6/1980 | Bailey | |
| 4,235,735 A | 11/1980 | Marco et al. | |
| 4,240,919 A | 12/1980 | Chapman | |
| 4,261,868 A | 4/1981 | Hora et al. | |
| 4,264,580 A | 4/1981 | Barberio | |
| 4,278,129 A | 7/1981 | Walton | |
| 4,287,080 A | 9/1981 | Siklosi | |
| 4,321,256 A | 3/1982 | Hasegawa et al. | |
| 4,350,680 A | 9/1982 | Harvey et al. | |
| 4,364,837 A | 12/1982 | Pader | |
| 4,391,722 A * | 7/1983 | Schwartz et al. | ............. 252/73 |
| 4,393,935 A | 7/1983 | Walton | |
| 4,470,923 A | 9/1984 | Koster | |
| 4,483,779 A | 11/1984 | Llenado et al. | |
| 4,507,219 A | 3/1985 | Hughes | |
| 4,525,291 A * | 6/1985 | Smith et al. | ............. 510/303 |
| 4,536,317 A | 8/1985 | Llenado et al. | |

(Continued)

FOREIGN PATENT DOCUMENTS

DE    2829022    1/1980

(Continued)

OTHER PUBLICATIONS

U.S. Appl. No. 12/137,647 "Mono-, Di and Polyol Phosphate Esters in Oral Care Formulations and Methods for Using Same", Futterer et al., filed Jun. 12, 2008.

(Continued)

*Primary Examiner*—Charles I Boyer
(74) *Attorney, Agent, or Firm*—Novak Druce + Quigg LLP

(57) ABSTRACT

A hydrophilized personal care formulation, which can be in the form of a hand or body soap (liquid or bar), lipstick, body wash, makeup remover, skin cleaner, hair conditioner, skin or hair moisturizer. The formulation employs an organophosphorus material or a mixture of an organophosphorus material, for example, mono-, di-, and polyol phosphate esters.

24 Claims, 1 Drawing Sheet

U.S. PATENT DOCUMENTS

| | | | |
|---|---|---|---|
| 4,536,318 A | 8/1985 | Cook et al. |
| 4,536,319 A | 8/1985 | Payne |
| 4,541,483 A | 9/1985 | Walton |
| 4,548,744 A | 10/1985 | Connor |
| 4,557,853 A | 12/1985 | Collins |
| 4,559,056 A | 12/1985 | Leigh et al. |
| 4,565,647 A | 1/1986 | Llenado |
| 4,579,681 A | 4/1986 | Ruppert et al. |
| 4,597,898 A | 7/1986 | Vander Meer |
| 4,599,188 A | 7/1986 | Llenado |
| 4,614,519 A | 9/1986 | Ruppert et al. |
| 4,627,977 A | 12/1986 | Gaffar et al. |
| 4,664,839 A | 5/1987 | Rieck |
| 4,702,857 A | 10/1987 | Gosselink |
| 4,711,730 A | 12/1987 | Gosselink et al. |
| 4,721,580 A | 1/1988 | Gosselink |
| 4,728,455 A | 3/1988 | Rerek |
| 4,734,099 A | 3/1988 | Cyprien |
| 4,746,456 A | 5/1988 | Kud et al. |
| 4,752,409 A | 6/1988 | Drapier et al. |
| 4,770,666 A | 9/1988 | Clauss |
| 4,801,395 A | 1/1989 | Chazard et al. |
| 4,813,482 A | 3/1989 | Walton |
| 4,836,949 A | 6/1989 | Klajnscek |
| 4,859,358 A * | 8/1989 | Gabriel et al. ............ 510/222 |
| 4,877,896 A | 10/1989 | Maldonado et al. |
| 4,886,609 A | 12/1989 | Walton |
| 4,891,160 A | 1/1990 | Vander Meer |
| 4,894,220 A | 1/1990 | Nabi et al. |
| 4,902,499 A | 2/1990 | Bolish, Jr. et al. |
| 4,933,101 A | 6/1990 | Cilley et al. |
| 4,968,451 A | 11/1990 | Scheibel et al. |
| 4,976,879 A | 12/1990 | Maldonado et al. |
| 5,015,466 A | 5/1991 | Parran, Jr. et al. |
| 5,019,373 A | 5/1991 | Carter et al. |
| 5,038,864 A | 8/1991 | Dunleavy |
| 5,064,553 A | 11/1991 | Dixit et al. |
| 5,098,590 A | 3/1992 | Dixit et al. |
| 5,104,643 A | 4/1992 | Grollier et al. |
| 5,114,606 A | 5/1992 | van Vliet et al. |
| 5,130,043 A | 7/1992 | Prince et al. |
| 5,160,450 A | 11/1992 | Okahara et al. |
| 5,236,615 A | 8/1993 | Trinh et al. |
| 5,280,117 A | 1/1994 | Kerschner et al. |
| 5,332,528 A | 7/1994 | Pan et al. |
| 5,370,865 A | 12/1994 | Yamagishi et al. |
| 5,405,542 A | 4/1995 | Trinh et al. |
| 5,413,727 A | 5/1995 | Drapier et al. |
| 5,415,807 A | 5/1995 | Gosselink et al. |
| 5,415,860 A | 5/1995 | Beucherie et al. |
| 5,510,042 A | 4/1996 | Hartman et al. |
| 5,510,306 A | 4/1996 | Murray |
| 5,534,197 A | 7/1996 | Scheibel et al. |
| 5,550,274 A | 8/1996 | Reierson |
| 5,554,781 A | 9/1996 | Reierson |
| 5,559,261 A | 9/1996 | Sivik |
| 5,565,145 A | 10/1996 | Watson et al. |
| 5,573,709 A | 11/1996 | Wells |
| 5,607,680 A | 3/1997 | Brissonnet et al. |
| 5,648,584 A | 7/1997 | Murray |
| 5,648,585 A | 7/1997 | Murray et al. |
| 5,686,024 A | 11/1997 | Dahanayake et al. |
| 5,710,121 A | 1/1998 | Tracy et al. |
| 5,798,326 A | 8/1998 | Goldstein et al. |
| 5,804,542 A | 9/1998 | Scheper et al. |
| 5,824,289 A | 10/1998 | Stoltz |
| 5,849,960 A | 12/1998 | Singleton et al. |
| 5,853,710 A | 12/1998 | Dehan et al. |
| 5,858,343 A | 1/1999 | Szymczak |
| 5,879,469 A * | 3/1999 | Avram ............ 134/25.2 |
| 5,902,574 A | 5/1999 | Stoner et al. |
| 5,902,778 A | 5/1999 | Hartmann et al. |
| 5,939,052 A | 8/1999 | White, Jr. et al. |
| 5,968,893 A | 10/1999 | Manohar et al. |
| 6,017,936 A | 1/2000 | Polson et al. |
| 6,136,221 A | 10/2000 | Reierson |
| 6,149,693 A | 11/2000 | Geib |
| 6,150,222 A | 11/2000 | Gardner et al. |
| 6,187,391 B1 | 2/2001 | Kataoka et al. |
| 6,220,352 B1 | 4/2001 | Walton |
| 6,222,077 B1 | 4/2001 | Singleton |
| 6,242,404 B1 | 6/2001 | Dahanayake et al. |
| 6,271,409 B1 | 8/2001 | Geib |
| 6,297,201 B1 | 10/2001 | Geib |
| 6,342,468 B1 | 1/2002 | Geib |
| 6,387,137 B1 | 5/2002 | Geib |
| 6,525,005 B1 * | 2/2003 | Kravitz et al. ............ 508/438 |
| 6,566,313 B1 | 5/2003 | Hohenstein et al. |
| 6,569,261 B1 | 5/2003 | Aubay et al. |
| 6,579,466 B1 | 6/2003 | David et al. |
| 6,593,288 B2 | 7/2003 | Aubay et al. |
| 6,767,410 B2 | 7/2004 | Aubey et al. |
| 6,767,560 B2 | 7/2004 | Paek |
| 6,864,314 B1 | 3/2005 | Yeung et al. |
| 6,924,260 B2 | 8/2005 | Aubay |
| 7,262,153 B2 | 8/2007 | Shpakoff et al. |
| 7,381,695 B2 * | 6/2008 | Minevski ............ 510/189 |
| 2003/0044469 A1 | 3/2003 | Petit et al. |
| 2003/0228339 A1 | 12/2003 | El-Nokaly et al. |
| 2004/0185027 A1 | 9/2004 | Reierson et al. |
| 2004/0247534 A1 | 12/2004 | Stoltz |
| 2005/0020466 A1 * | 1/2005 | Man et al. ............ 510/392 |
| 2005/0184273 A1 | 8/2005 | Morelli et al. |
| 2006/0088482 A1 | 4/2006 | Wulknitz et al. |
| 2006/0093559 A1 | 5/2006 | Fabry |
| 2006/0135384 A1 | 6/2006 | Luu et al. |
| 2006/0217286 A1 | 9/2006 | Geoffroy et al. |
| 2007/0145617 A1 | 6/2007 | Finney et al. |
| 2007/0166243 A1 | 7/2007 | Yoshida et al. |
| 2008/0028986 A1 | 2/2008 | Futterer et al. |
| 2008/0095719 A1 | 4/2008 | Herrmann et al. |
| 2008/0220031 A1 | 9/2008 | Wunsch et al. |

FOREIGN PATENT DOCUMENTS

| | | |
|---|---|---|
| EP | 0011984 | 6/1980 |
| EP | 0066915 | 12/1982 |
| EP | 0132043 | 1/1985 |
| EP | 0132046 | 1/1985 |
| EP | 0219048 | 4/1987 |
| EP | 0488868 | 6/1992 |
| EP | 0561656 | 9/1993 |
| EP | 0909809 | 4/1999 |
| EP | 1196523 | 4/2002 |
| EP | 1196527 | 4/2002 |
| EP | 1196528 | 4/2002 |
| FR | 2236926 | 2/1975 |
| FR | 2334698 | 7/1977 |
| GB | 849433 | 9/1960 |
| GB | 1314897 | 4/1973 |
| GB | 1475798 | 6/1977 |
| GB | 1498520 | 1/1978 |
| GB | 1537288 | 12/1978 |
| GB | 1578930 | 11/1980 |
| GB | 2 192 194 A | 1/1988 |
| GB | 2 283 036 A | 4/1995 |
| GB | 2 283 755 A | 5/1995 |
| JP | 047547 | 1/1992 |
| JP | 6313271 | 11/1994 |
| JP | 2005-013929 | 1/2005 |
| WO | 9532272 | 11/1995 |
| WO | 9532997 | 12/1995 |
| WO | 9623859 | 8/1996 |
| WO | 9623860 | 8/1996 |

| | | |
|---|---|---|
| WO | 9623861 | 8/1996 |
| WO | 97/42287 A1 | 11/1997 |
| WO | 9742288 | 11/1997 |
| WO | 9838973 | 9/1998 |
| WO | 9841505 | 9/1998 |

OTHER PUBLICATIONS

U.S. Appl. No. 12/137,823 "Method for Recovering Crude Oil from a Subterranean Formation", Futterer et al., filed Jun. 12, 2008.

U.S. Appl. No. 12/137,738 "Hard Surface Cleaning Composition with Hydrophilizing Agent and Method for Cleaning Hard Surfaces", Futterer et al., filed Jun. 12, 2008.

U.S. Appl. No. 12/138,030 "Detergent Composition with Hydrophilizing Soil-Release Agent and Methods for Using Same" Futterer et al., filed Jun. 12, 2008.

Office Action mailed Oct. 3, 2008 in U.S. Appl. No. 12/138,030.

Office Action mailed Oct. 10, 2008 in U.S. Appl. No. 12/137,823.

Office Action mailed Oct. 3, 2008 in U.S. Appl. No. 12/137,647.

Notice of Allowance mailed Nov. 13, 2008 in U.S. Appl. No. 12/137,738.

* cited by examiner

MONO-, DI- AND POLYOL PHOSPHATE ESTERS IN PERSONAL CARE FORMULATIONS

CROSS REFERENCE TO RELATED APPLICATIONS

This claims the benefit of U.S. Provisional Patent Application No. 60/943,487 filed Jun. 12, 2007 which is incorporated by reference in its entirety.

FIELD OF THE INVENTION

This invention relates to a hydrophilized personal care formulation, which can be in the form of a hand or body soap (liquid or bar), lipstick, bodywash, makeup remover, skin cleaner, hair conditioner, skin or hair moisturizer. The present invention employs mono-, di-, and polyol phosphate esters (like polyethylene glycol phosphate esters, polypropylene glycol phosphate esters, glycerin phosphate esters).

BACKGROUND OF THE INVENTION

In personal care applications, consumers are increasingly demanding formulations that provide multiple benefits. The present invention discloses the use of mono-, di-, and polyol phosphate esters which when used in personal care formulations can provide wide ranging benefits such as, but not limited to, unique sensory experience, enhanced moisturization, increased conditioning, improved delivery of active ingredients and compatibility. These molecules can provide many of the above benefits listed either by themselves or in certain cases can have synergistic effects with principal functioning agents resulting in increased efficacy or a reduction in the amount of the agent used. These molecules can provide these benefits either while in use and/or after rinsing which makes them unique and opens the possibility to be used in both "leave on" and "rinse off" products.

Currently the following methodologies have been adopted to overcome some of the problems of multiple benefits: amphipilic molecules such as surfactants for foaming, cleansing and lathering; oils and humectants such as glycerin to provide moisturizing, polymers for aiding the deposition of active ingredients or pertinent materials (such as silicones).

Materials that have a low surface energy, such as, for example, polyolefin polymers, have hydrophobic surfaces. The hydrophobic properties of such materials are not desirable in some applications and methods for hydrophilizing low surface energy substrates, including treatment with surfactants and/or high energy treatment, are known. Each of these methods has significant limitations. Surfactant treatments tend to wash off when a treated substrate is exposed to water and the charges imparted to the surface of a treated substrate by high energy treatment tend, particularly in the case of a thermoplastic polymer substrate, to dissipate. The hydrophilic properties of such surfactant treated substrates and high energy treated substrates thus tend to exhibit limited durability. Furthermore, the surfactants that are rinsed off of a treated substrate by exposure to water alter the properties of the water, such as lowering the surface tension, which may also be undesirable.

SUMMARY OF THE INVENTION

The present invention uses mono-, di-, and polyol phosphate esters (like PEG phosphate esters, PPG phosphate esters, and glycerin phosphate esters) to provide multiple benefits to typical personal care formulations. These molecules are expected to adsorb on to the skin from a formulation as they are applied and render many of the benefits listed in this disclosure. The concentrations in which they may be used can vary depending on the intended purpose and the amount of benefit desired. These molecules are expected to remain adsorbed to the skin, scalp or any other body part applied and will have a reduced tendency to be washed or rinsed away. It is indeed unique that these molecules, with low molecular weights and a hydrophilic nature, would prefer to remain adsorbed at an interface instead of be washed away in the aqueous bulk. The adsorption of these molecules onto the skin, scalp or other body parts as well as the benefits they render can be readily measured. For example, measurements such as visual dryness, corneometry, TEWL (transepidermal water loss) can provide information about the dryness/moisturization of the skin. Panel tests can verify the unique sensory benefits rendered and model surfaces can be used to demonstrate the adsorption of these molecules as well as the enhanced adsorption of active ingredients and certain principal functioning agents.

In a first aspect, the present invention is directed to a personal care composition, comprising:

(a) an acceptable vehicle; and (b) an ionic hydrophyllizing agent comprising (b)(I) an organophosphorus material selected from:

(b)(I)(1) organophosphorus compounds according to structure (I):

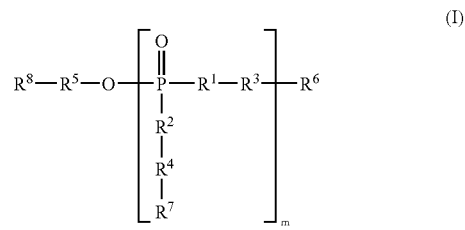

(I)

wherein:
each $R^1$ is and each $R^2$ is independently absent or O, provided that at least one of $R^1$ and $R^2$ is O,
each $R^3$ is independently alkyleneoxy, poly(alkyleneoxy), which may optionally, be substituted on one or more carbon atom of such alkyleneoxy, or poly(alkyleneoxy) group by hydroxyl, alkyl, hydroxyalkyl, alkoxy, alkenyl, aryl, or aryloxy,
$R^5$ is and each $R^4$ is independently absent or alkyleneoxy, poly(alkyleneoxy), which may optionally, be substituted on one or more carbon atom of such alkyleneoxy, or poly(alkyleneoxy) group by hydroxyl, alkyl, hydroxyalkyl, alkoxy, alkenyl, aryl, or aryloxy,
$R^6$ and $R^8$ are each and each $R^7$ is independently H, or $(C_1-C_{30})$hydrocarbon, which hydrocarbon may optionally be substituted on one or more carbon atoms by hydroxyl, fluorine, alkyl, alkenyl or aryl and/or interrupted at one or more sites by an O, N, or S heteroatom, or $-POR^9R^{10}$,
$R^9$ and $R^{10}$ are each independently hydroxyl, alkoxy, aryloxy, or $(C_1-C_{30})$hydrocarbon, which hydrocarbon may optionally be substituted on one or more carbon atoms by hydroxyl, fluorine, alkyl, alkenyl or aryl and/or interrupted at one or more sites by an O, N, or S heteroatom, and
m is an integer of from 1 to 5, (b)(I)(2) salts of organophosphorus compounds according to structure (I), (b)(I)(3) condensation reaction products of two or more molecules of one or more organophosphorus compounds according to structure (I), and (b)(I)(4) mixtures comprising two or more of the compounds, salts, and/or reaction products of (b)(I)(1), (b)(I)(2), and (b)(I)(3).

If desired the composition may further comprise:

(b)(II) a vinyl alcohol material selected from:
(b)(II)(1) polymers comprising monomeric units according to structure (I-a):

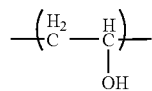

(I-a)

(b)(II)(2) salts of polymers (b)(II)(1), (b)(II)(3) reaction products of two or more molecules of one or more polymers (b)(II)(1), and (b)(II)(4) mixtures comprising two or more of the polymers, salts, and/or reaction products of (b)(II)(1), (b)(II)(2), and (b)(II)(3).

Unique sensory experience: On using products containing the molecules consumers should notice certain unique sensory benefits. These could include lubriciousness and a more silky and smooth feel without a feeling of tackiness or stickiness. This unique sensory benefit can be differentiated when compared to humectants such as glycerin which may provide moisturization but tend to give a sticky feeling to the consumer. Similarly, biopolymers while improving deposition may tend to leave a tacky feeling which can be avoided by the use of these molecules. Sulfate based surfactants tend to be irritating to the skin while these molecules are mild and non irritating. The unique sensory experience may be well exploited in many personal care applications such as, but not limited to, body washes, hand washes, facial creams, lotions, shampoos, hair styling products, antiaging and sunscreen applications. In certain applications such as baby products, the nonirritating and the quasi amphipilic nature may be well suited.

Enhanced moisturization: The use of these molecules should provide a more moisturized skin with reduced dryness. While oils and glycerin are traditionally used to enhance moisturization, it is indeed surprising that molecules such as these can provide mositurization by themselves. Also these molecules may provide a synergistic effect when used with traditional moisturizers resulting in reduced dryness. The use of these molecules could also enhance the regulation of the natural moisture of the skin or scalp. These effects could occur in products such as body washes or shaving gels where a well moisturized skin can have a significant benefit to the consumer.

Improving skin properties: the use of these molecules could potentially improve the appearance of the skin by improving the hydration of the skin. They could also form a barrier or protection layer which can help reduce environmental damage. One may also expect improved exfoliation of the skin particularly when these molecules are used in facial lotions or products.

Deposition of actives: The inclusion of these molecules is expected to increase the deposition of active ingredients and principal functioning agents. For example, use of these molecules in shampoos could improve the deposition of silicone or other conditioning and styling agents, in antiaging creams the overall efficacy may be improved due to a synergy between a well nourished, hydrated skin and the active. In some instances the molecules themselves may be able to provide a degree of antiaging and exfoliation benefit.

Increased compatibility: One of the benefits of this system may be their ability to be used in a wide variety of formulation types (aqueous, emulsions, creams, lotions, gels etc) in a wide variety of physico chemical conditions and using a wide variety of additives, fragrances and active ingredients and yet rendering many of the benefits listed.

These molecules are relatively inexpensive and easy to manufacture in comparison to many polymers used for surface treatments. They are considered non-toxic, non-irritant to skin and biodegradable.

DETAILED DESCRIPTION OF EMBODIMENTS OF THE INVENTION

Figure 1:
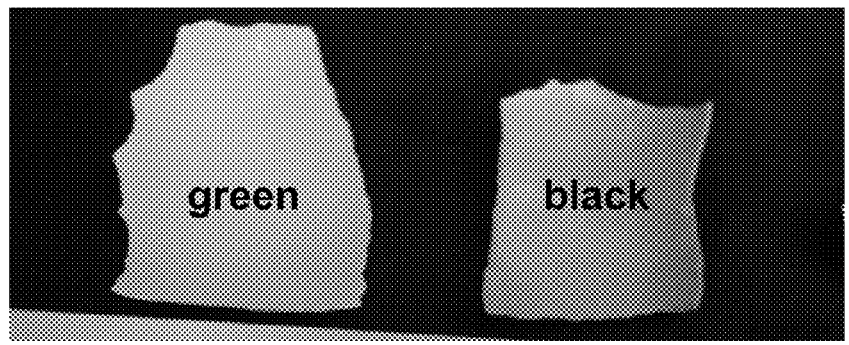
FIG. 1 shows a photograph of egg-shell brushed with commercial toothpaste, then stained with green (left) and black (right) tea, and then brushed again with commercial toothpaste.

As used herein, the terminology "hydrophobic surface" means a surface that exhibits a tendency to repel water and to thus resist being wetted by water, as evidenced by a water contact angle of greater than or equal to 70°, more typically greater than or equal to 90°, and/or a surface free energy of less than or equal to about 40 dynes/cm.

As used herein, the terminology "hydrophilic surface" means a surface that exhibits an affinity for water and to thus be wettable by water, as evidenced by a water contact angle of less than 70°, more typically less than 60° and/or a surface energy of greater than about 40 dynes/cm, more typically greater than or equal to about 50 dynes/cm.

As used herein in reference to a hydrophobic surface, the term "hydrophilizing" means rendering such surface more hydrophilic and thus less hydrophobic, as indicated by a decreased water contact angle. One indication of increased hydrophilicity of a treated hydrophobic surface is a decreased water contact angle with a treated surface compared to the water contact angle with an untreated surface.

A used herein in reference to a substrate, the terminology "water contact angle" means the contact angle exhibited by a droplet of water on the surface as measured by a conventional image analysis method, that is, by disposing a droplet of water on the surface, typically a substantially flat surface, at 25° C., photographing the droplet, and measuring the contact angle shown in the photographic image.

Surface energy is estimated using the Young equation:

$$\cos(\theta) \ast \gamma_{lv} = \gamma_{sv} - \gamma_{sl}$$

with the contact angle θ, the interfacial energy $y_{sv}$ between the solid and the vapor phase, the interfacial energy $\gamma_{sl}$ between the solid and the liquid phase, and the interfacial energy $\gamma_{lv}$ between the liquid and the vapor phase, and $\gamma_{sv}$ represents the surface energy of the solid.

As used herein, "molecular weight" in reference to a polymer or any portion thereof, means to the weight-average molecular weight ("$M_w$") of said polymer or portion, wherein $M_w$ of a polymer is a value measured by gel permeation chromatography, static light scattering, viscometry, or a number of other standard techniques and $M_w$ of a portion of a polymer is a value calculated according to known techniques from the amounts of monomers, polymers, initiators and/or transfer agents used to make the said portion.

As used herein, the notation "$(C_n-C_m)$" in reference to an organic group or compound, wherein n and m are integers, means that the group or compound contains from n to m carbon atoms per such group or compound.

Compositions for beauty and personal care include a wide variety of products, such as shampoos and formulations for hand and/or body wash, hair and skin conditioners, hand cream and makeup removal product. A variety of personal care compositions are described by U.S. Pat. No. 6,864,314, herein incorporated by reference in its entirety.

Organophosphorus Material

The present invention includes personal care compositions comprising a surface active agent and a hydrophyilizing agent comprising organophosphorus material selected from:
(1) organophosphorus compounds according to structure (I):

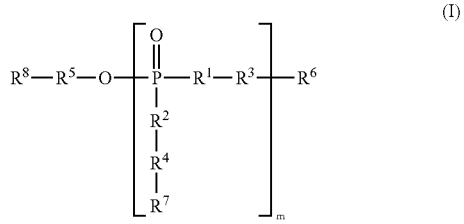

(I)

wherein:
each $R^1$ is and each $R^2$ is independently absent or O, provided that at least one of $R^1$ and $R^2$ is O,
each $R^3$ is independently alkyleneoxy, poly(alkyleneoxy), which may optionally, be substituted on one or more carbon atom of such alkyleneoxy, or poly(alkyleneoxy) group by hydroxyl, alkyl, hydroxyalkyl, alkoxy, alkenyl, aryl, or aryloxy,
$R^5$ is and each $R^4$ is independently absent or alkyleneoxy, poly(alkyleneoxy), which may optionally, be substituted on one or more carbon atom of such alkyleneoxy, or poly(alkyleneoxy) group by hydroxyl, alkyl, hydroxyalkyl, alkoxy, alkenyl, aryl, or aryloxy,
$R^6$ and $R^3$ are each and each $R^7$ is independently H, or ($C_1-C_{30}$)hydrocarbon, which hydrocarbon may optionally be substituted on one or more carbon atoms by hydroxyl, fluorine, alkyl, alkenyl or aryl and/or interrupted at one or more sites by an O, N, or S heteroatom, or —$POR^9R^{10}$,
$R^9$ and $R^{10}$ are each independently hydroxyl, alkoxy, aryloxy, or ($C_1-C_{30}$)hydrocarbon, which hydrocarbon may optionally be substituted on one or more carbon atoms by hydroxyl, fluorine, alkyl, alkenyl or aryl and/or interrupted at one or more sites by an O, N, or S heteroatom, and m is an integer of from 1 to 5,
(2) salts of organophosphorus compounds according to structure (I),
(3) condensation reaction products of two or more molecules of one or more organophosphorus compounds according to structure (I), and
(4) mixtures comprising two or more of the compounds, salts, and/or reaction products of (1), (2), and (3).

Suitable organophosphorus material are also described in U.S. provisional patent application Nos. 60/842,265, filed Sep. 5, 2006 and 60/812,819, filed Jun. 12, 2006, both incorporated herein by reference.

As used herein, the term "alkyl" means a monovalent saturated straight chain or branched hydrocarbon radical, typically a monovalent saturated ($C_1-C_{30}$)hydrocarbon radical, such as for example, methyl, ethyl, n-propyl, iso-propyl, n-butyl, sec-butyl, t-butyl, pentyl, or n-hexyl, which may optionally be substituted on one or more of the carbon atoms of the radical. In one embodiment, an alkyl radical is substituted on one or more carbon atoms of the radical with alkoxy, amino, halo, carboxy, or phosphono, such as, for example, hydroxymethyl hydroxyethyl, methoxymethyl, ethoxymethyl, isopropoxyethyl, aminomethyl, chloromethyl or trichloromethyl, carboxyethyl, or phosphonomethyl.

As used herein, the term "hydroxyalkyl" means an alkyl radical that is substituted on one of its carbon atoms with a hydroxyl group.

As used herein, the term "alkoxyl" means an oxy radical that is substituted with an alkyl group, such as for example, methoxyl, ethoxyl, propoxyl, isopropoxyl, or butoxyl, which may optionally be further substituted on one or more of the carbon atoms of the radical.

As used herein, the term "cycloalkyl" means a saturated cyclic hydrocarbon radical, typically a ($C_3-C_8$) saturated cyclic hydrocarbon radical, such as, for example, cyclohexyl or cyclooctyl, which may optionally be substituted on one or more of the carbon atoms of the radical.

As used herein, the term "alkenyl" means an unsaturated straight chain, branched chain, or cyclic hydrocarbon radical that contains one or more carbon-carbon double bonds, such as, for example, ethenyl, 1-propenyl, or 2-propenyl, which may optionally be substituted on one or more of the carbon atoms of the radical.

As used herein, the term "aryl" means a monovalent unsaturated hydrocarbon radical containing one or more six-membered carbon rings in which the unsaturation may be represented by three conjugated double bonds, such as for example, phenyl, naphthyl, anthryl, phenanthryl, or biphenyl, which may optionally be substituted one or more of carbons of the ring. In one embodiment, an aryl radical is substituted on one or more carbon atoms of the radical with hydroxyl, alkenyl, halo, haloalkyl, or amino, such as, for example, methylphenyl, dimethylphenyl, hydroxyphenyl, chlorophenyl, trichloromethylphenyl, or aminophenyl.

As used herein, the term "aryloxy" means an oxy radical that is substituted with an aryl group, such as, for example, phenyloxy, methylphenyl oxy, isopropylmethylphenyloxy.

As used herein, the indication that a radical may be "optionally substituted" or "optionally further substituted" means, in general, that is unless further limited, either explicitly or by the context of such reference, that such radical may be substituted with one or more inorganic or organic substituent groups, such as, for example, alkyl, alkenyl, aryl, aralkyl, alkaryl, a hetero atom, or heterocyclyl, or with one or more functional groups that are capable of coordinating to metal ions, such as hydroxyl, carbonyl, carboxyl, amino, imino, amido, phosphonic acid, sulphonic acid, or arsenate, or inorganic and organic esters thereof, such as, for example, sulphate or phosphate, or salts thereof.

As used herein, the terminology "$(C_x-C_y)$" in reference to an organic group, wherein x and y are each integers, indicates that the group may contain from x carbon atoms to y carbon atoms per group.

In one embodiment, $R^6$ and $R^8$ are each and each $R^7$ is independently H, $(C_1-C_{30})$alkyl, $(C_1-C_{30})$alkenyl, or $(C_7-C_{30})$alkaryl.

In one embodiment, each $R^1$ and each $R^2$ is O, and the organophosphorus compound is selected from:
(II)(1) an organophosphate ester according to structure (II):

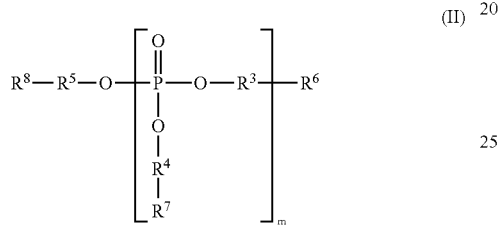

(II)

wherein $R^3$, $R^4$, $R^5$, $R^6$, $R^7$, $R^8$, and m are each as described above,
(II)(2) salts of organophosphorus compounds according to structure (II),
(II)(3) condensation reaction products of two or more molecules of one or more organophosphorus compounds according to structure (II), and
(II)(4) mixtures comprising two or more of the compounds, salts, and/or reaction products of (II)(1), (II)(2), and (II)(3).

In one embodiment, each $R^1$ is absent, each $R^2$ is O, and the organophosphorus compound is selected from:
(III)(1) an organophosphonate ester according to structure (III):

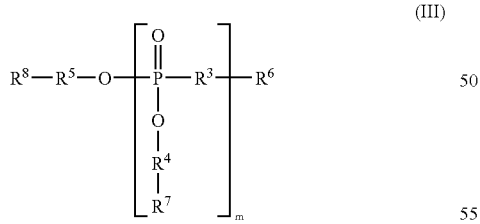

(III)

wherein $R^3$, $R^4$, $R^5$, $R^6$, $R^7$, $R^8$, and m are each as described above,
(III)(2) salts of organophosphorus compounds according to structure (III),
(III)(3) condensation reaction products of two or more molecules of one or more organophosphorus compounds according to structure (III), and
(III)(4) mixtures comprising two or more of the compounds, salts, and/or reaction products of (III)(1), (III)(2), and (III)(3).

In one embodiment, each $R^1$ is O, each $R^2$ is absent, and the organophosphorus compound is selected from:
(IV)(1) an organophosphonate ester according to structure (IV):

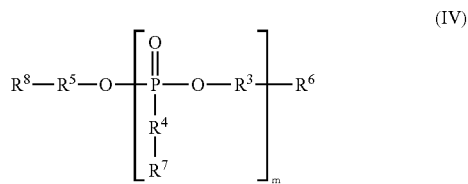

(IV)

wherein $R^3$, $R^4$, $R^5$, $R^6$, $R^7$, $R^8$, and m are each as described above,
(IV)(2) salts of organophosphorus compounds according to structure (IV),
(IV)(3) condensation reaction products of two or more molecules of one or more organophosphorus compounds according to structure (IV), and
(IV)(4) mixtures comprising two or more of the compounds, salts, and/or reaction products of (IV)(1), (IV)(2), and (IV)(3).

In one embodiment, each $R^3$ is a divalent radical according to structure (V), (VI), (VII), or (VIII):

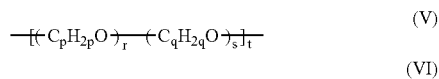

(V)

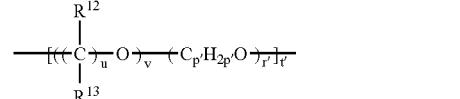

(VI)

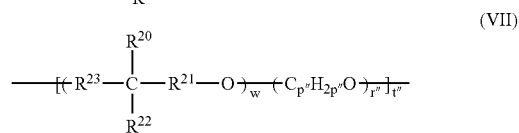

(VII)

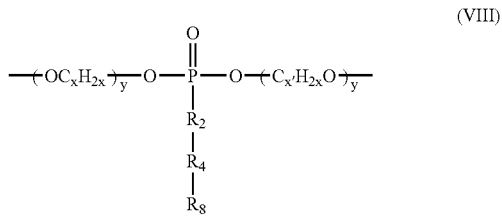

(VIII)

wherein:
each $R^{12}$ and each $R^{13}$ is independently H, hydroxyl, alkyl, hydroxyalkyl, alkoxy, alkenyl, aryl, aryloxy, or two $R^{12}$ groups that are attached to the adjacent carbon atoms may be fused to form, together with the carbon atoms to which they are attached, a $(C_6-C_8)$ hydrocarbon ring,
$R^{20}$ is H, hydroxyl, alkyl, hydroxyalkyl, alkoxy, alkenyl, aryl, or aryloxy
$R^{22}$ is hydroxyl or hydroxyalkyl, provided that $R^{20}$ and $R^{22}$ are not each hydroxyl,
$R^{23}$ and $R^{21}$ are each independently methylene or poly (methylene),
p, p', p", q, and x are each independently integers of from 2 to 5,
each r, s, r', r", and y is independently a number of from 0 to 25, provided that at least one of r and s is not 0,
u is an integer of from 2 to 10,
v and w are each numbers of from 1 to 25, and
t, t', and t'' are each numbers of from 1 to 25,
provided that the product of the quantity (r+s) multiplied times t is less than or equal to about 100, the product of the quantity (v+r') multiplied times t' is less than or equal to about 100, and the product of the quantity (w+r'') multiplied time t'' is less than or equal to about 100.

In one embodiment, each $R^4$ and each $R^5$ is independently absent or a divalent radical according to structure (V), (VI), or (VII), wherein $R^{12}$, $R^{13}$, $R^{20}$, $R^{21}$, $R^{22}$, $R^{23}$, p, p', p'', q, r, r', r'', s, t, t'', t, u, v, w, x, and y are as described above.

In one embodiment, each $R^3$ is independently a divalent radical according to structure (V), (VI), or (VII) wherein $R^{12}$, $R^{13}$, $R^{20}$, $R^{21}$, $R^{22}$, $R^{23}$, p, p', p'', q, r, r', r'', s, t, t'', t, u, v, w, x, and y are as described above, and $R^4$ and $R^5$ are each independently absent or $R^3$.

In one embodiment, each $R^3$ is independently a divalent radical according to structure (V), wherein p is 2, 3, or 4, r is an integer from 1 to 25, s is 0, t is an integer of from 1 to 2, and $R^4$ and $R^5$ are each independently absent or $R^3$.

In one embodiment, each $R^3$ is independently a divalent radical according to structure (VI), wherein the $R^{12}$ groups are fused to form, including the carbon atoms to which they are attached, a ($C_6$-$C_8$) hydrocarbon ring, each $R^{13}$ is H, p' is 2 or 3, u is 2, v is an integer of from 1 to 3, r' is an integer from 1 to 25, t' is an integer of from 1 to 25, the product of the quantity (v+r') multiplied times t'' is less than or equal to about 100, more typically less than or equal to about 50, and $R^4$ and $R^5$ are each independently absent or $R^3$.

In one embodiment, each $R^3$ is independently a divalent radical according to structure (VII), wherein $R^{20}$ is hydroxyl or hydroxyalkyl, $R^{22}$ is H, alkyl, hydroxyl, or hydroxyalkyl, provided that $R^{20}$ and $R^{22}$ are not each hydroxyl, $R^{21}$ and $R^{23}$ are each independently methylene, di(methylene), or tri(methylene), w is 1 or 2, p'' is 2 or 3, r'' is an integer of from 1 to 25, t'' is an integer of from 1 to 25, the product of the quantity (w+r'') multiplied times t'' is less than or equal to about 100, more typically less than or equal to about 50, and $R^4$ and $R^5$ are each independently absent or $R^3$.

In one embodiment of the organophosphorus compound according to structure (II)
$R^6$ and $R^8$ are each and each $R^7$ is independently H or ($C_1$-$C_{30}$)hydrocarbon, which hydrocarbon may optionally be substituted on one or more carbon atoms by hydroxyl, fluorine, alkyl, alkenyl or aryl and/or interrupted at one or more sites by an O, N, or S heteroatom, or —$POR^9R^{10}$, more typically, $R^6$, $R^8$, and each $R^7$ are each H,
$R^4$ and $R^5$ are each absent,
each $R^3$ is independently a divalent radical according to structure (V), (VI), or (VII), and
m is an integer of from 1 to 5.

In one embodiment of the organophosphorus compound according to structure (II):
$R^6$, $R^8$, and each $R^7$ are each H,
$R^4$ and $R^5$ are each absent,
each $R^3$ is independently a divalent radical according to structure (V),
each p is independently 2, 3, or 4, more typically 2 or 3,
each r is independently a number of from 1 to about 100, more typically from
2 to about 50,
each s is 0,
each t is 1, and
m is an integer of from 1 to 5.

In one embodiment, the organophosphorus material is selected from:
(X)(1) organophosphorus compounds according to structure (IX):

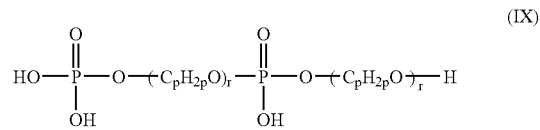

wherein:
p is 2, 3, or 4, more typically 2 or 3,
r is a number of from 4 to about 50,
(IX)(2) salts organophosphorus compounds according to structure (IX), and
(IX)(3) mixtures comprising two or more of the compounds and/or salts of (IX)(1) and (IX)(2).

In one embodiment of the organophosphorus compound according to structure (II):
$R^6$, $R^8$, and each $R^7$ are each H,
$R^4$ and $R^5$ are each absent,
each $R^3$ is independently a divalent radical according to structure (VI),
the $R^{12}$ groups are fused to form, including the carbon atoms to which they are attached, a ($C_6$-$C_8$)hydrocarbon ring,
each $R^{13}$ is H
p' is 2 or 3,
u is 2,
v is 1,
r' is a number of from 1 to 25,
t' is a number of from 1 to 25,
the product of the quantity (v+r') multiplied times t' is less than or equal to about 100, and
m is an integer of from 1 to 5.

In one embodiment of the organophosphorus compound according to structure (II):
$R^6$, $R^8$, and each $R^7$ are each H,
$R^4$ and $R^5$ are each absent,
each $R^3$ is independently a divalent radical according to structure (VII),
$R^{20}$ is hydroxyl or hydroxyalkyl,
$R^{22}$ is H, alkyl, hydroxyl, or hydroxyalkyl,
$R^{23}$ and $R^{21}$ are each independently methylene, di(methylene), or tri(methylene),
w is 1 or 2,
p'' is 2 or 3,
r'' is a number of from 1 to 25,
t'' is a number of from 1 to 25
the product of the quantity (w+r'') multiplied times t'' is less than or equal to about 100, and
m is an integer of from 1 to 5.

In one embodiment, the organophosphorus compound is according to structure (III), each $R^3$ is a divalent radical according to structure (V) with s=0 and t=1, $R^4$ and $R^5$ are each absent, and $R^6$, $R^7$, and $R^8$ are each H.

In one embodiment, the organophosphorus compound is according to structure (IV), wherein $R^3$ and $R^5$ are each according to structure (V), with s=0 and t=1, and $R^6$ and $R^8$ are each H.

In one embodiment, the organophosphorus material (b)(I) comprises a condensation reaction product of two or more molecules according to structure (I).

In one embodiment, the organophosphorus material (b)(I) comprises a condensation reaction product of two or more molecules according to structure (I) in the form of a linear molecule, such as, for example, a linear condensation reaction product according to structure (X), formed by condensation of a molecule according to structure (II) with a molecule according to structure (IV):

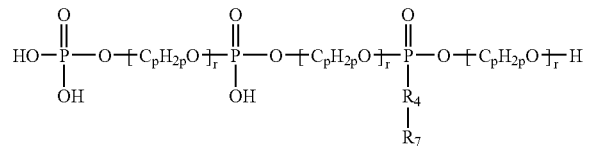

(X)

wherein $R^4$, $R^7$, p, r are each as described above.

In one embodiment, the organophosphorus material (b)(I) comprises a condensation reaction product of two or more molecules according to structure (I) in the form of a crosslinked network. A portion of an exemplary crosslinked condensation reaction product network is illustrated by structure (XI):

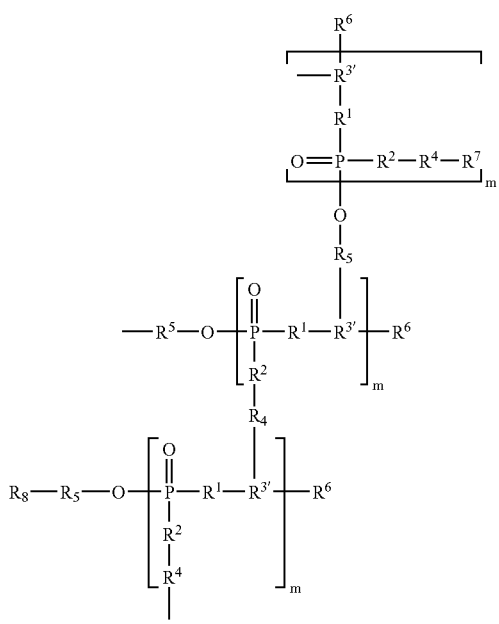

(XI)

wherein $R^1$, $R^2$, $R^4$, $R^5$, $R^6$, $R^7$, $R^8$, and m are each as described above, and each $R^3$ is independently a residue of an $R^3$ group of a compound according to structure (I), as described above, wherein the $R^3$ group is a alkyleneoxy or poly(alkyleneoxy) moiety substituted with hydroxyl-, hydroxyalkyl-, hydroxyalkyleneoxy- or hydroxypoly(alkyleneoxy)- on one or more carbon atoms of the alkyleneoxy or poly(alkyleneoxy) moiety, and —$R^{3'}$—$R^4$— and —$R^{3'}$—$R^5$— each represent a respective linkage formed by condensation of such an $R^3$ group and a —$R^{3'}$—$R^5$— or —$R^8$—$R^5$— group of molecules of another molecule of a compound according to structure (I).

In one embodiment, the organophosphorus material (b)(I) comprises a condensation reaction product of two or more molecules according to structure (I) and the condensation reaction product forms a covalently crosslinked organophosphorus network. Typically the solubility of the covalently crosslinked organophosphorus network in water is less than that of the organophosphorus compound according to structure (I), more typically, the covalently crosslinked organophosphorus network is substantially insoluble in water.

As used herein, the term "salts" refers to salts prepared from bases or acids including inorganic or organic bases and inorganic or organic acids.

In one embodiment, the organophosphorus material (b)(I) is in the form of a salt that comprises an anion derived (for example, by deprotonation of a hydroxyl or a hydroxyalkyl substituent) from of an organophosphorus compound according to structure (I) and one or more positively charged counterions derived from a base.

Suitable positively charged counterions include inorganic cations and organic cations, such as for example, sodium cations, potassium cations, calcium cations, magnesium cations, copper cations, zinc cations, ammonium cations, tetraalkylammonium cations, as well as cations derived from primary, secondary, and tertiary amines, and substituted amines.

In one embodiment, the cation is a monovalent cation, such as for example, $Na^+$, or $K^+$.

In one embodiment, the cation is a polyvalent cation, such as, for example, $Ca^{+2}$, $Mg^{+2}$, $Zn^{+2}$, $Mn^{+2}$, $Cu^{+2}$, $Al^{+3}$, $Fe^{+2}$, $Fe^{+3}$, $Ti^{+4}$, $Zr^{+4}$, in which case the organophosphorus compound may be in the form of a "salt complex" formed by the organophosphorus compound and the polyvalent cation. For organophosphorus compound having two or more anionic sites, e.g., deprotonated hydroxyl substituents, per molecule, the organophosphorus compound-polyvalent cation complex can develop an ionically crosslinked network structure. Typically the solubility of the ionically crosslinked organophosphorus network in water is less than that of the organophosphorus compound according to structure (I), more typically, the ionically crosslinked organophosphorus network is substantially insoluble in water.

Suitable organophosphorus compounds can be made by known synthetic methods, such as by reaction of one or more compounds, each having two or more hydroxyl groups per molecule, with phosphoric acid, polyphosphoric acid, and or phosphoric anhydride, such as disclosed, for example, in U.S. Pat. Nos. 5,550,274, 5,554,781, and 6,136,221.

In one embodiment, cations are immobilized on a water insoluble substrate to form a water insoluble cationic particle and the hydrophilizing layer further comprises cationic particles. Suitable substrates include inorganic oxide particles, including for example, oxides of single elements, such as cerium oxide, titanium oxide, zirconium oxide, halfnium oxide, tantalum oxide, tungsten oxide, silicon dioxide, and bismuth oxide, zinc oxide, indium oxide, and tin oxide, and mixtures of such oxides, as well as oxides of mixtures of such elements, such as cerium-zirconium oxides. Such particle may exhibit a mean particle diameter ("$D_{50}$") of from about 1 nanometer ("nm") to about 50 micrometers ("µm"), more typically from about 5 to about 1000 nm, even more typically from about 10 to about 800 nm, and still more typically from about 20 to about 500 nm, as determined by dynamic light scattering or optical microscopy. In one embodiment, aluminum cations are immobilized on silica particles.

Vinyl Alcohol Material

In one embodiment, the personal care composition comprises a vinyl alcohol material (b)(II).

In one embodiment, which offers improved solubility in water and improved processability, the vinyl alcohol material (b)(II) comprises a polymer that comprises monomeric units according to structure (I-a) (a "vinyl alcohol polymer").

In one embodiment, the vinyl alcohol polymer and exhibits a weight average molecular weight of greater than or equal to about 10,000, more typically from about 10,000 to about 100,000, even more typically from about 10,000 to about 30,000. In an alternative embodiment, which offers improved durability, the vinyl alcohol polymer a weight average molecular weight of greater than or equal to about 100,000, more typically form about 100,000 to about 200,000. In another embodiment, which offers a balance between processability and durability, the vinyl alcohol polymer exhibits a weight average molecular weight of greater than or equal to about 50,000, more typically from about 50,000 to about 150,000, even more typically from about 80,000 to about 120,000.

In one embodiment, the vinyl alcohol polymer is made by polymerizing a vinyl ester monomer, such as for example, vinyl acetate, to form a polymer, such as a poly(vinyl acetate) homopolymer or a copolymer comprising monomeric units derived from vinyl acetate, having a hydrocarbon backbone and ester substituent groups, and then hydrolyzing at least a portion of the ester substituents groups of the polymer to form hydroxy-substituted monomeric units according to structure (I-a). In one embodiment, which offers improved solubility in water and improved processability, the vinyl alcohol polymer exhibits a degree of hydrolysis of greater than or equal to about 88%, more typically from about 88% to about 95%. As used herein in reference to a vinyl alcohol polymer that is made by hydrolyzing a polymer initially having a hydrocarbon backbone and ester substituent groups, the term "degree of hydrolysis" means the relative amount, expressed as a percentage, of vinyl ester-substituted monomeric units that were hydrolyzed to form hydroxy-substituted monomeric units. In another embodiment, which offers improved solubility in water and improved durability, the vinyl alcohol polymer exhibits a degree of hydrolysis of greater than or equal to about 99%. In yet another embodiment, which offers a compromise between solubility in water and durability, the polymer exhibits a degree of hydrolysis from about 92 to about 99%.

In one embodiment, the vinyl alcohol polymer has a linear polymeric structure. In an alternative embodiment, the vinyl alcohol polymer has a branched polymeric structure.

In one embodiment, the vinyl alcohol polymer is a vinyl alcohol homopolymer that consists solely of monomeric units according to structure (I-a).

In one embodiment, the vinyl alcohol polymer is a vinyl alcohol copolymer that comprises monomeric units having a structure according to structure (I-a) and further comprises comonomeric units having a structure other than structure (I-a). In one embodiment, the vinyl alcohol polymer is a copolymer that comprises hydroxy-substituted monomeric units according to (I-a) and ester substituted monomeric units and is made by incomplete hydrolysis of a vinyl ester homopolymer.

In one embodiment a vinyl alcohol copolymer comprises greater than or equal to about 50 mole % ("mol %"), more typically greater or equal to than about 80 mol %, monomeric units according to structure (I-a) and less than about 50 mol %, more typically less than about 20 mol %, comonomeric units having a structure other than structure (I-a).

As described above, vinyl alcohol polymers having monomeric units according to structure (I-a) are typically derived from polymerization of vinyl ester monomers and subsequent hydrolysis of vinyl ester-substituted monomeric units of the polymer. Suitable vinyl alcohol copolymers are typically derived by copolymerization of the vinyl ester monomer with any ethylenically unsaturated monomer that is copolymerizable with the vinyl ester monomer, including for example, other vinyl monomers, allyl monomers, acrylic acid, methacrylic acid, acrylic ester monomers, methacrylic ester monomers, acrylamide monomers, and subsequent hydrolysis of at least a portion of the ester-substituted monomeric units to form hydroxy-substituted monomeric units according to structure (I-a).

In one embodiment, the vinyl alcohol polymer comprises monomeric units according to structure (I-a) and further comprises hydrophilic monomeric units other than the monomeric according to structure (I-a). As used herein, the term "hydrophilic monomeric units" are those wherein homopolymers of such monomeric units are soluble in water at 25° C. at a concentration of 1 wt % homopolymer, and include, for example, monomeric units derived from, for example, hydroxy($C_1$-$C_4$)alkyl(meth)acrylates, (meth)acrylamide, ($C_1$-$C_4$)alkyl(meth)acrylamides, N,N-dialkyl-acrylamides, alkoxylated (meth)acrylates, poly(ethylene glycol)-mono methacrylates and poly(ethyleneglycol)-monomethylether methacrylates, hydroxy($C_1$-$C_4$)acrylamides and methacrylamides, hydroxyl($C_1$-$C_4$)alkyl vinyl ethers, N-vinylpyrrole, N-vinyl-2-pyrrolidone, 2- and 4-vinylpyridine, ethylenically unsaturated carboxylic acids having a total of 3 to 5 carbon atoms, amino($C_1$-$C_4$)alkyl, mono($C_1$-$C_4$)alkylamino($C_1$-$C_4$)alkyl, and di($C_1$-$C_4$)alkylamino($C_1$-$C_4$)alkyl (meth)acrylates, allyl alcohol, dimethylaminoethyl methacrylate, dimethylaminoethylmethacrylamide.

In one embodiment, the vinyl alcohol polymer comprises monomeric units according to structure (I-a) and further comprises hydrophobic monomeric units. As used herein, the term "hydrophobic monomeric units" are those wherein homopolymers of such monomeric units are insoluble in water at 25° C. at a concentration of 1 wt % homopolymer, and include, for example, monomeric units derived from ($C_1$-$C_{18}$)alkyl and ($C_5$-$C_{18}$)cycloalkyl (meth)acrylates, ($C_5$-$C_{18}$) alkyl(meth)acrylamides, (meth)acrylonitrile, vinyl ($C_1$-$C_{18}$) alkanoates, ($C_2$-$C_{18}$)alkenes, ($C_2$-$C_{18}$)haloalkenes, styrene, ($C^1$-$C_6$)alkylstyrenes, ($C_4$-$C_{12}$)alkyl vinyl ethers, fluorinated ($C_2$-$C_{10}$)alkyl(meth)acrylates, ($C_3$-$C_{12}$)perfluoroalkylethylthiocarbonylaminoethyl (meth)acrylates, (meth)acryloxyalkylsiloxanes, N-vinylcarbazole, ($C_1$-$C_{12}$) alkyl maleic, fumaric, itaconic, and mesaconic acid esters, vinyl acetate, vinyl propionate, vinyl butyrate, vinyl valerate, chloroprene, vinyl chloride, vinylidene chloride, vinyltoluene, vinyl ethyl ether, perfluorohexyl ethylthiocarbonylaminoethyl methacrylate, isobornyl methacrylate, trifluoroethyl methacrylate, hexa-fluoroisopropyl methacrylate, hexafluorobutyl methacrylate, tristrimethylsilyloxysilylpropyl methacrylate, and 3-methacryloxypropylpentamethyldisiloxane.

As used herein, the term "(meth)acrylate" means acrylate, methacrylate, or acrylate and methacrylate and the term (meth)acrylamide" means acrylamide, methacrylamide or acrylamide and methacrylamide.

In one embodiment, the polymer comprising monomeric units according to structure (I-a) a random copolymer. In another embodiment, the copolymer comprising monomeric units according to structure (I-a) is a block copolymer.

Methods for making suitable vinyl alcohol polymers are known in the art. In one embodiment, a polymer comprising monomeric units according to structure (I-a) is made by polymerizing one or more ethylenically unsaturated monomers, comprising at least one vinyl ester monomer, such vinyl acetate, by known free radical polymerization processes and subsequently hydrolyzing at least a portion of the vinyl ester monomeric units of the polymer to make a polymer having the desired degree of hydrolysis. In another embodiment, the polymer comprising monomeric units according to structure (I-a) is a copolymer made by known controlled free radical polymerization techniques, such as reversible addition fragmentation transfer (RAFT), macromolecular design via interchange of xanthates (MADIX), or atom transfer reversible polymerization (ATRP).

In one embodiment, the vinyl alcohol polymer is made by known solution polymerization techniques, typically in an aliphatic alcohol reaction medium.

In another embodiment, the vinyl alcohol polymer is made by known emulsion polymerization techniques, in the presence of one or more surfactants, in an aqueous reaction medium.

In one embodiment, the vinyl alcohol material comprises a microgel made by crosslinking molecules of a vinyl alcohol polymer.

In one embodiment the vinyl alcohol material comprises a salt, such as a sodium or potassium salt, of a vinyl alcohol polymer.

In one embodiment, the hydrophilizing layer comprises one or more poly(vinyl alcohol) polymers. Poly(vinyl alcohol) polymers are manufactured commercially by the hydrolysis of poly(vinyl acetate). In one embodiment, the poly(vinyl alcohol) has a molecular weight of greater than or equal to about 10,000 (which corresponds approximately to a degree of polymerization of greater than or equal to about 200), more typically from about 20,000 to about 200,000 (which corresponds approximately to a degree of polymerization of from about 400 to about 4000, wherein the term "degree of polymerization" means the number of vinyl alcohol units in the poly(vinyl alcohol) polymer. In one embodiment, the poly(vinyl alcohol) has a degree of hydrolysis of greater than or equal about 50, more typically greater than or equal about 88%.

In one embodiment, the hydrophilizing layer comprises an organophosphorus material (b)(I) and a vinyl alcohol material (b)(II), more typically, based on 100 parts by weight (pbw) of the hydrophilizing layer, from greater than 0 pbw to less than 100 pbw, more typically from about 0.1 pbw to about 99.9 pbw, and even more typically from about 1 pbw to about 99 pbw, organophosphorus material (b)(I), from greater than 0 pbw to less than 100 pbw, more typically from about 0.1 pbw to about 99.9 pbw, and even more typically from about 1 pbw to about 99 pbw, vinyl alcohol material (b)(II).

Liquid Carrier

In one embodiment, the treatment composition of the present invention comprises the organophosphorus material (b)(I) and a liquid carrier.

In one embodiment, the liquid carrier is an aqueous carrier comprising water and the treatment solution is in the form of a solution, emulsion, or dispersion of the organophosphorus material and additives. In one embodiment, the liquid carrier comprises water and a water miscible organic liquid. Suitable water miscible organic liquids include saturated or unsaturated monohydric alcohols and polyhydric alcohols, such as, for example, methanol, ethanol, isopropanol, cetyl alcohol, benzyl alcohol, oleyl alcohol, 2-butoxyethanol, and ethylene glycol, as well as alkylether diols, such as, for example, ethylene glycol monoethyl ether, propylene glycol monoethyl ether and diethylene glycol monomethyl ether.

As used herein, terms "aqueous medium" and "aqueous media" are used herein to refer to any liquid medium of which water is a major component. Thus, the term includes water per se as well as aqueous solutions and dispersions.

Compositions

In one embodiment, the personal care composition comprises, based on 100 parts by weight ("pbw") of the composition, from about 0.1 to about 20 pbw, more typically, from about 1 to about 5 pbw, organophosphorus material, and from about 80 to 99 pbw, more typically, from about 90 to about 98 pbw, liquid carrier.

In one embodiment, the personal care composition further comprises, based on 100 parts by weight ("pbw") of the composition, from about 0.01 to about 10 pbw, more typically, from about 0.1 to about 5 pbw colloidal inorganic particles.

In one embodiment, the personal care composition further comprises, based on 100 parts by weight ("pbw") of the composition, from about 0.01 to about 2 pbw, more typically, from about 0.1 to about 0.5 pbw poly(vinyl alcohol).

In one embodiment, the personal care composition further comprises and from about 0.0001 to about 1 pbw, more typically, from about 0.001 to about 0.1 pbw multivalent cationic particles.

In one embodiment, the personal care composition comprises, based on 100 parts by weight ("pbw") of the composition, from about 0.1 to about 20 pbw, more typically, from about 1 to about 5 pbw, vinyl alcohol material (b)(II), and from about 80 to 99 pbw, more typically, from about 90 to about 98 pbw, liquid carrier.

In one embodiment, the personal care composition of the present invention comprises an organophosphorus material (b)(I) and a vinyl alcohol material (b)(II) and a liquid carrier.

In one embodiment, the personal care composition comprises, based on 100 parts by weight ("pbw") of the composition, from about 0.1 to about 20 pbw, more typically, from about 1 to about 5 pbw, organophosphorus material (b)(I), from about 0.1 to about 20 pbw, more typically, from about 1 to about 5 pbw, vinyl alcohol material (b)(II), and from about 80 to 99 pbw, more typically, from about 90 to about 98 pbw, liquid carrier.

The composition according to the invention can be provided in any form and can be used in multiple ways.

Thus, it can be in the form of a viscoelastic or viscous medium to be deposited as such, in particular by applying,
  directly on the surfaces to be cleaned or rinsed, or
  on a sponge or another substrate (woven or nonwoven article made of cellulose, for example) before being applied to the surface to be treated.
It can be in the form of:
  a viscoelastic or viscous medium to be diluted in water (optionally with the addition of another solvent) before being applied to body;
  a viscoelastic or viscous medium held in a water-soluble bag.
  a foam,
  an aerosol,
  a viscoelastic or viscous medium absorbed on an absorbent substrate made of an article which is woven or nonwoven in particular (wipe),
  a solid, for example as a tablet or granules, optionally held in a water-soluble bag, it being possible for the composition to represent all or part of the tablet or granules.

The composition forming the subject matter of the invention can comprise, depending on its application, from 0.001 to 10% of its weight of at least one of the phosphate esters.

The pH of the composition or the pH of use of the composition according to the invention can vary, depending on the applications and the specific body part to be treated. The pH of the compositions is not critical and can be in the range of from about 2 to about 12, preferably from about 4 to about 10 and most preferably from about 6 to about 8. The pH can be adjusted using a buffer such as, but not limited to, citric acid.

The composition can be employed in an amount such that, after optional rinsing and after drying, the amount of phosphate esters deposited on the surface is typically from 0.0001 to 10 mg/m$^2$, for example, 0.001 to 5 mg/m$^2$, of surface treated.

Unless otherwise indicated, when molar mass is referred to, the reference will be to the weight-average molar mass, expressed in g/mol. The latter can be determined by aqueous gel permeation chromatography (GPC), light scattering (DLS or alternatively MALLS), or a number of other standard techniques, with an aqueous eluent or an organic eluent (for example dimethylacetamide, dimethylformamide, and the like), depending on the composition of the polymer.

Additional Ingredients

In addition to the organophosphorus material of the present invention, beauty care and personal care products, such as skin and hair conditioners, shampoos and soaps for hand and/or body wash, of the present invention contain adjunct ingredients. Additional background on such products is provided by PCT application serial number PCT/US98/04474, filed Mar. 6, 1998 and published as WO 98/38973, as well as by U.S. Pat. No. 6,864,314, each of which is incorporated herein by reference in its entirety.

The organophosphorus material described herein may also be used in other personal care products which also have additional ingredients. For example, the material may be used in place of similar materials in hand creams (as described by U.S. Patent Application Publication No. 2003/0044469), makeup removers or skin cleaners (as described by U.S. Pat. No. 5,607,680), or in hand soaps (as described by U.S. Patent Application Publication NO. 2006/0135384). Each of the documents discussed in this paragraph are expressly incorporated by reference in their entireties.

Pearlescent Additives

Pearlescent additives, also known as pearlizing agents, are often added to beauty and personal care products such as hair and skin care products to provide a pearly appearance to the products. Chemicals which are tiny (micron size) needles or platelets often exhibit this pearly appearance. Materials which exhibit this effect are ethylene glycol mono- and distearate, TiO$_2$ coated mica, bismuth oxychloride, and natural mother of pearl. Many organic materials exhibit this pearlescence provided they can be produced in an appropriate needle or platelet shape. Ethylene glycol distearate (EGDS) or ethylene glycol monostearate (EGMS) are the most commonly utilized pearlizing agents.

A stable, mild free flowing cold pearlizing concentrate is typically prepared using i) a pearlizing agent of this invention, preferably a glycol stearate; ii) a nonionic surfactant; iii) an amphoteric surfactant emulsifier and stabilizer, iv) a glycol emulsifier and v) water; to obviate the use of cocodiethanolamide and provide excellent compatibility with any ionic surfactant. The concentrate will typically be essentially free of anionic surfactants such that the concentrate is compatible with essentially any ionic surfactants that may be used in the personal care product to which this concentrate is added.

The pearlizing agent comprises from about 5% to about 40%, preferably from about 10% to about 30% and most preferably from about 15% to about 25%, by weight based on the total weight of the concentrate.

The pearlizing agent can be selected from the group consisting of hydroxyl stearate, polyethylene glycol mono- and di-stearates, ethylene glycol mono- and distearates, stearic monoethanolamide, and mixtures thereof. The preferred agents are polyethylene glycol mono- and distearates, and ethylene glycol mono- and di-stearates. The most preferred pearlizing agents for use are: ethylene glycol mono- and di-stearates.

The fatty acid based member must be derived from a fatty acid feedstock (which includes free fatty acids, carboxylate salts, fatty mono-, di- and/or tri-glycerides) which consists of at least about 90% by weight of octadecanoic acid, i.e. the saturated fatty acid having one carboxyl group (or derivative thereof) and a seventeen carbon alkyl tail covalently bonded thereto. Stearic acid is available commercially in different grades, typically containing at least some portion of palmitic acid, i.e. the saturated fatty acid having one carboxyl group, and a fifteen carbon alkyl tail covalently bonded thereto. For example, stearic acid is available in grades of 37.5% (nominal) and 42.5% (nominal) purity. Thus, those grades of stearic acid wherein less than about 90% of the fatty acid chains are octadecanoic acid will not be useful in making the fatty acid based member used herein, unless the stearic acid is first purified to remove a sufficient number of species which are not derived from octadecanoic acid. A useful grade of stearic acid is the 95% (nominal) grade the CTFA specifications of which are 92.5% to 97.5% stearic acid and a maximum of 5% palmitic acid. A fatty acid comprised of 90% stearic acid and 10% palmitic acid should also be useful.

The pearlizing agent is most useful as a concentrate with other components, e.g. those other components as described in published Patent Cooperation Treaty Application WO 98/38973, published Sep. 11, 1998, the disclosure of which is incorporated herein by reference in its entirety.

Non-Ionic Surfactant

A second potential component of the beauty and personal care product is a nonionic surfactant, which includes the organophosphorus material of the invention. This surfactant can function as an emulsifier and stabilizer in the formulation. The term "nonionic surfactant" as utilized herein encompasses mixtures of nonionic surfactants.

Examples of useful nonionic surfactants can additionally include condensates of ethylene oxide with a hydrophobic moiety which has an average hydrophilic lipophilic balance (HLB) between about 8 to about 16, and more preferably, between about 10 and about 12.5. These surfactants include the condensation products of primary or secondary aliphatic alcohols having from about 8 to about 24 carbon atoms, in either straight or branched chain configuration, with from about 2 to about 40, and preferably between about 2 and about 9 moles of ethylene oxide per mole of alcohol.

In a preferred embodiment the aliphatic alcohol comprises between about 9 and about 18 carbon atoms and is ethoxylated with between about 3 and about 12 moles of ethylene oxide per mole of aliphatic alcohol. Especially preferred are the about 12 to about 15 carbon primary alcohol ethoxylates containing about 5 to about 9 moles of ethylene oxide per mole of alcohol. One such material is commercially sold under the trade name NEODOL 25-9 by Shell Chemical Company. Other commercial nonionic surfactants include NEODOL 25-6.5 and NEODOL 25-7 sold by Shell Chemical Company.

Other suitable nonionic surfactants include the condensation products of about 6 to about 12 carbon atom alkyl phenols with about 3 to about 30, and preferably between about 5 and 14 moles of ethylene oxide. Examples of such surfactants are sold under the trade names IGEPAL CO 530, IGEPAL CO 630, IGEPAL CO720 and IGEPAL CO 730 by Rhodia, Inc. Still other suitable nonionic surfactants are described in U.S. Pat. No. 3,976,586. To the extent necessary, this patent is expressly incorporated by reference.

Most preferred for use are mixed linear alcohol ethoxylates such as Laureth-7 sold as RHODASURF L-790 by Rhodia, Inc.

The nonionic surfactant is incorporated in the cold pearlizing concentrate in an amount of from about 3% to about 30%; preferably from about 8% to about 25% and most preferably from about 10% to 20%, based on the total weight of the concentrate.

Amphoteric Surfactant

An amphoteric surfactant comprises the third potential component of personal care products of the present invention. The term "amphoteric surfactant" as utilized herein encompasses one or more amphoteric surfactants such as mixtures of amphoteric surfactants. Preferably, amphoteric surfactants known as the betaines, their derivatives, and mixtures thereof are incorporated to provide an enhanced pearlizing effect.

Examples of suitable amphoteric surfactants include the alkali metal, alkaline earth metal, ammonium or substituted ammonium salts of alkyl amphocarboxy glycinates and alkyl amphocarboxypropionates, alkyl amphodipropionates, alkyl amphodiacetates, alkyl amphoglycinates and alkyl amphopropionates wherein alkyl represents an alkyl group having 6 to 20 carbon atoms. Other suitable amphoteric surfactants include alkyl iminopropionates, alkyl iminodipropionates and alkyl amphopropylsulfonates having between 12 and 18 carbon atoms; alkyl betaines and amidopropyl betaines and alkyl sultaines and alkylamidopropylhydroxy sultaines wherein alkyl represents an alkyl group having 6 to 20 carbon atoms.

Particularly useful amphoteric surfactants include both mono and dicarboxylates such as those of the formulae:

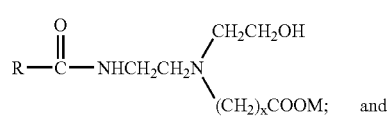
(I)

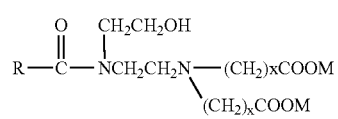
(II)

wherein R is an alkyl group of 6-20 carbon atoms, x is 1 or 2 and M is hydrogen or sodium. Mixtures of the above structures are particularly preferred.

Other formulae for the above amphoteric surfactants include the following:

Alkyl Betaines

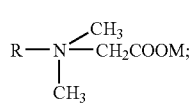
(III)

Amidopropyl Betaines

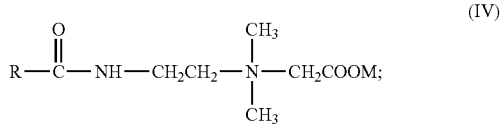
(IV)

Alkyl Sultaines

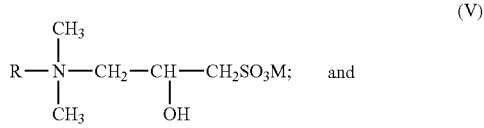
(V)

Alkyl Amidopropylhydroxy Sultaines

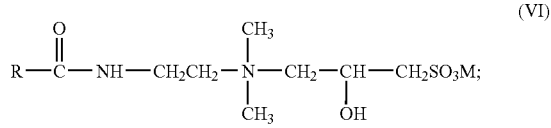
(VI)

where R is a alkyl group of 6-20 carbon atoms and M is potassium, sodium or a monovalent cation.

Of the above amphoteric surfactants, particularly preferred are the alkali salts of alkyl amphodipropionates, alkyl amphodiacetates, alkyl amphoglycinates, alkyl amphopropyl sulfonates and alkyl amphopropionates wherein alkyl represents an alkyl group having 6 to 20 carbon atoms. Even more preferred are compounds wherein the alkyl group is derived from coconut oil or is a lauryl group, for example cocoamphodipropionate. Such cocoamphodipropionate surfactants are commercially sold under the trademarks MIRANOL C2M-SF CONC. and MIRANOL FBS by Rhodia, Inc.

Other commercially useful amphoteric surfactants include:
- cocoamphoacetate (sold under the trademarks MIRANOL ULTRA C-32 and MIRAPON FA),
- cocoamphopropionate (sold under the trademarks MIRANOL CMSF CONC. and MIRAPON FAS),
- cocoamphodiacetate (sold under the trademarks MIRANOL C2M CONC. and MIRAPON FB),
- lauroamphoacetate (sold under the trademarks MIRANOL HM CONC. and MIRAPON LA),
- lauroamphodiacetate (sold under the trademarks MIRANOL H2M CONC. and MIRAPON LB),
- lauroamphodipropionate (sold under the trademarks MIRANOL H2M-SF CONC. AND MIRAPON LBS),
- lauroamphodiacetate obtained from a mixture of lauric and myristic acids (sold under the trademark MIRANOL BM CONC.), and
- cocoamphopropyl sulfonate (sold under the trademark MIRANOL CS CONC.)
- caproamphodiacetate (sold under the trademark MIRANOL S2M CONC.),
- caproamphoacetate (sold under the trademark MIRANOL SM CONC.),
- caproamphodipropionate (sold under the trademark MIRANOL S2M-SF CONC.), and
- stearoamphoacetate (sold under the trademark MIRANOL DM).

The most preferred amphoteric surfactant for use is cocoamphoacetate. It can be present from 0% to 10% based on the total weight of the concentrate. Preferably, cocoamphoacetate will comprise from about 1% to about 7% and most preferably from about 2% to about 4% of the concentrate.

Also useful herein are the betaines and amidobetaines which are compounds of the general structure:

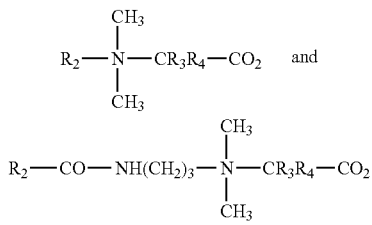

respectively wherein $R_2$ is $C_8$-$C_{22}$ alkyl or alkenyl; $R_3$ is H or $C_1$-$C_4$ alkyl; and $R_4$ is H or $C_1$-$C_4$ alkyl.

The betaines useful herein include the high alkyl betaines such as cocodimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, and lauryl bis-(2-hydroxypropyl)alpha-carboxyethyl betaine. The sulfobetaines are also preferred and may be represented by cocodimethyl sulfopropyl betaine, stearyldimethyl sulfopropyl betaine, lauryl dimethyl sulfoethyl betaine, lauryl bis-(2-hydroxy-ethyl)sulfopropyl betaine and mixtures thereof. A particularly preferred composition utilizes cocoamidopropyl betaine.

Most preferably, the amphoteric surfactant can be cocoamphoacetate and cocoamidopropyl betaine acting as amphoteric co-emulsifiers.

The amphoteric surfactant can be present from about 2% to about 20% weight percent based on the total weight of the pearlizing concentrate. Preferably, the amphoteric will comprise from about 4% to about 16%, most preferably from about 6% to about 10%, of the pearlizing concentrate.

Glycol Emulsifier

The fourth potential component consists of a glycol emulsifier. Propylene glycol (1,2, and 1,3) and other alcohols such as 1,3-butylene glycol, 2,3-butylene glycol, ethylene glycol and mixtures thereof are useful emulsifiers. The glycol emulsifier can be present from 0% to about 15%, preferably from about 1% to about 10% and most preferably from about 2% to about 5%.

Water

For the fifth component, the remainder is water, preferably deionized. Generally, water is added in an amount of from about 20% to about 70%, preferably from about 30% to about 60%, and most preferably from about 40% to about 55% based on the total weight of the concentrate.

Additional Components

Non-essential optional components can be utilized in the concentrates of the present invention as a convenient means of incorporation into beauty and personal care products. Such conventional optional ingredients are well known to those skilled in the art, e.g., preservatives such as benzyl alcohol, methyl paraben, propyl paraben and imidazolidinyl urea; thickeners and viscosity modifiers such as block polymers of ethylene oxide and propylene oxide, e.g. ANTAROX F-88 (Rhodia, Inc.), sodium chloride, sodium sulfate, polyvinyl alcohol, and ethyl alcohol; pH adjusting agents such as citric acid, succinic acid, phosphoric acid, sodium hydroxide, sodium carbonate; perfumes; natural oils and petroleum derivatives, dyes; and sequestering agents such as disodium ethylenediamine tetra-acetate. Such agents generally are used individually at levels of from 0% to about 2%, preferably from 0.01% to about 1.0% by weight of the concentrate.

The pH of the concentrate compositions is not critical and can be in the range of from about 2 to about 12, preferably from about 4 to about 10 and most preferably from about 6 to about 8. The pH can be adjusted using a buffer such as, but not limited to, citric acid.

The order of addition to the mixing tank of the individual components of the concentrate is not critical nor is the reasonably elevated temperature; however, preferably the water and pearlizing agent are intimately blended at from about 50° to about 90° C., more preferably from about 70° to about 80° C. with high agitation until the pearlizing agent is emulsified. The nonionic and amphoteric surfactants are then blended into the mix until the mixture is clear. The mixture is then allowed to cool to room temperature. Generally, the concentrate can be stored at a temperature of from about 0° C. to about 45° C., preferably from about 15° C. to about 35° C. for at least one day and preferably two days in order to fully develop its pearlizing characteristics.

Silicone Compounds

The personal care compositions may further comprise a silicone compound. As referred to herein, a silicone compound is a nonfunctionalized siloxane having a viscosity of from about 5 to about 600,000 cs (centistoke), and preferably from about 350 to about 10,000 cs, at 25° C. The so-called "rigid silicones", as described in U.S. Pat. No. 4,902,499, herein incorporated by reference, having a viscosity above 600,000 cs at 20° C., e.g., 700,000 cs plus, and a weight average molecular weight of at least about 500,000, also are useful. The silicone compound is typically a polydimethylsiloxane, typically a linear polydimethylsiloxane terminated at each end with a trimethylsilyl group. The silicone compound can be a dimethicone as specified by the CTFA, i.e. an alpha, omega-trimethylsilyl-polydimethylsiloxane having a viscosity at 25° C. of at least 25 centistokes and less than 60,000 centistokes. The silicone compound is typically used in the context of a shampoo and is added to the composition in an amount sufficient to impart improved combing and improved feel, such as softness, to the hair after shampooing.

The silicone hair conditioning agent for use herein will preferably have viscosity of from about 1,000 to about 2,000,000 centistokes at 25° C., more preferably from about 10,000 to about 1,800,000, even more preferably from about 100,000 to about 1,500,000. The viscosity can be measured by means of a glass capillary viscometer as set forth in Dow Corning Corporate Test Method CTM0004, Jul. 20, 1970, or a conventional rheometer or viscometer.

The silicone hair conditioning agent will be used in the shampoo compositions hereof at levels of from about 0.1% to about 10% by weight of the composition, preferably from about 0.5% to about 8%, more preferably from about 1% to about 5%.

Suitable insoluble, nonvolatile silicone fluids include polyalkyl siloxanes, polyaryl siloxanes, polyalkylaryl siloxanes, polyether siloxane copolymer and mixtures thereof. However, other insoluble, nonvolatile silicone fluids having hair conditioning properties may be used. The term "nonvolatile" as used herein shall mean that the silicone material exhibits very low or no significant vapor pressure at ambient conditions, as is well understood in the art. The term "silicone fluid" shall mean flowable silicone materials having a viscosity of less than 1,000,000 centistokes at 25° C. Generally, the viscosity of the fluid will be between about 5 and 1,000,000 centistokes at 25° C., preferably between about 10 and about 100,000. The term "silicone", as used herein, shall be synonymous with the term "polysiloxane".

The nonvolatile polyalkylsiloxane fluids that may be used include, for example, polydimethyl siloxanes. These siloxanes are available, for example, from the General Electric Company as a VISCASIL series and from Dow Corning as the Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified dimethylpolysiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

Silicone fluids hereof also include polyalkyl or polyaryl siloxanes with the structure shown in U.S. Pat. No. 5,573,709, the disclosure of which is incorporated herein by reference, herein R is alkyl or aryl, and x is an integer from about 7 to about 8,000 may be used. "A" represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

References disclosing suitable silicone fluids include U.S. Pat. No. 2,826,551, Geen; U.S. Pat. No. 3,964,500, Drakoff, issued Jun. 22, 1976; U.S. Pat. No. 4,364,837, Pader; and British Patent 849,433, Woolston. All of these patents are incorporated herein by reference. Also incorporated herein by reference is Silicon Compounds distributed by Petrarch Systems, Inc., 1984. This reference provides an extensive (though not exclusive) listing of suitable silicone fluids.

Another silicone material that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, Chemistry and Technology of Silicones, N.Y.: Academic Press 1968. Also describing silicone gums are General Electric Silicone Rubber Product Data Sheets SE 30, SE 33, SE 54 and SE 76. All of these described references are incorporated herein by reference. The "silicone gums" will typically have a mass molecular weight in excess of about 200,000, generally between about 200,000 and about 1,000,000. Specific examples include polydimethylsiloxane, (polydimethylsiloxane)(methylvinylsiloxane) copolymer, poly(dimethylsiloxane) (diphenyl siloxane)(methylvinylsiloxane) copolymer and mixtures thereof.

Preferably the silicone hair conditioning agent comprises a mixture of a polydimethylsiloxane gum, having a viscosity greater than about 1,000,000 centistokes and polydimethylsiloxane fluid having a viscosity of from about 10 centistokes to about 100,000 centistokes, wherein the ratio of gum to fluid is from about 30:70 to about 70:30, preferably from about 40:60 to about 60:40.

Another optional ingredient that can be included in the silicone conditioning agent is silicone resin. Silicone resins are highly crosslinked polymeric siloxane systems. The crosslinking is introduced through the incorporation of trifunctional and tetrafunctional silanes with monofunctional or difunctional, or both, monomer units during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen: silicon atoms is at least about 1.2:1.0. Silanes used in the manufacture of silicone resins include monomethyl-, dimethyl-, monophenyl-, diphenyl-, methylphenyl-, monovinyl-, and methylvinyl-chlorosilanes, and tetra-chlorosilane, with the methyl-substituted silanes being most commonly utilized. Preferred resins are offered by General Electric as GE SS4230 and SS4267. Commercially available silicone resins will generally be supplied in an unhardened form in a low viscosity volatile or nonvolatile silicone fluid. The silicone resins for use herein should be supplied and incorporated into the present compositions in such unhardened form, as will be readily apparent to those skilled in the art.

Background material on silicones including sections discussing silicone fluids, gums, and resins, as well as manufacture of silicones, can be found in Encyclopedia of Polymer Science and Engineering, Volume 15, Second Edition, pp 204-308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid component to the silicone resin component is from about 4:1 to about 400:1, preferably this ratio is from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above.

Rheology Modifiers

The treatment composition may optionally further comprise, based on 100 pbw weight of the composition up to about 10 pbw of other components, such as, salts, sugars, surfactants, and rheology modifiers. Suitable salts include, for example, NaCl, KCl, NH$_3$Cl, N(C$_2$H$_5$)$_3$Cl. Suitable sugars include monosaccharides and polysaccharides, such as, for example, glucose or guar gum. Suitable rheology modifiers include, for example but not limited to, alkali swellable polymers, such as acrylic acid polymers, hydrogen bridging rheology modifiers, such as carboxymethylcellulose or hydroxyethylcellulose, and hydrophobic associative thickeners, such as hydrophobically modified cellulose derivatives and hydrophobically modified alkoxylated urethane polymers.

Shampoo Surfactants

When the organophosphorus material is used in a shampoo, the shampoo will typically contain a detersive surfactant. These include anionic, cationic, nonionic surfactants, amphoteric surfactants, zwitterionic surfactants. Examples of anionic surfactants are described in U.S. Pat. No. 5,573,709, the entire disclosure of which is incorporated by reference. However, the shampoo will typically be essentially free of anionic surfactants, e.g. contain less than 0.5% by weight of species that can properly be characterized as anionic surfactants. If the formulation does not include an anionic surfactant, cationic detersive surfactants can also be used.

Nonionic detersive surfactants which can be used include those broadly defined as compounds produced by the condensation of alkylene oxide groups (hydrophilic in nature) with an organic hydrophobic compound, which may be aliphatic or alkyl aromatic in nature. Examples of preferred classes of nonionic detersive surfactants are:

1. The polyethylene oxide condensates of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of about 2,500 to about 3,000, are satisfactory.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

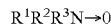

$R^1R^2R^3N \rightarrow O$ wherein R1 contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

5. Long chain tertiary phosphine oxides corresponding to the following general formula:

RR'R"P→O wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide. 3,6,9,-trioxaoctadecyldimethylphosphine oxide, cetyldimethylphosphine oxide, 3-dodecoxy-2-hydroxypropyldi (2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleydimethylphosphine oxide, 2-hydroxydodecyldimethylphosphine oxide.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include: octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Zwitterionic detersive surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is: found in U.S. Pat. No. 5,573,709, which is incorporated herein by reference, wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:
4-[N,N-di(2-hydroxyethyl)-N-octadecylammonio]-butane-1-carboxylate;
5-[S-3-hydroxypropyl-5-hexadecylsulfonio]-3-hydroxypentane-1-sulfate;
3-[P, P-diethyl-P-3,6,9-trioxatetradexocylphosphonio]-2-hydroxy-propane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxy-pentane-1-sulfate.

Other zwitterionics such as betaines can also useful in the present invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, and lauryl bis-(2-hydroxypropyl)alphacarboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl)sulfopropyl betaine and the 1 like; amidobetaines and amidosulfobetaines, wherein the RCONH $(CH_2)_3$ radical is attached to the nitrogen atom of the betaine are also useful in this invention. Preferred betaines for use in the present compositions are cocoamidopropyl betaine, cocobetaine, lauryl amidopropyl betaine, and oleyl betaine.

Examples of amphoteric detersive surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "MIRANOL"™ and described in U.S. Pat. No. 2,528,378. Another detersive surfactant optional for use in the compositions of the present invention is cocoamphocarboxy glycinate.

The most preferred shampoos of the present invention contain combinations of amphoteric surfactants, zwitterionic surfactants, and nonionic surfactants and are essentially free of anionic surfactants. The shampoos typically contain from about 0% to about 6% of amphoteric surfactants, about 0% to about 8% of zwitterionic surfactants, from 0% to about 14% of ethoxylated alkyl sulfates, and from about 0% to about 10% of an optional anionic surfactant surfactants, e.g. about 3% to about 7% alkyl sulfates, with a total surfactant level of from about 10% to about 25%.

Additional Shampoo and Soap Ingredients

The formulated shampoo and soap systems of the present invention can contain a variety of non-essential optional components suitable for rendering such compositions more acceptable. Such conventional optional ingredients are well known to those skilled in the art, e.g., preservatives such as benzyl alcohol, methyl paraben, propyl paraben and imidazolidinyl urea; cationic surfactants such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; thickeners and viscosity modifiers such as, but not limited to, block polymers of ethylene oxide and propylene oxide, e.g. ANTAROX F-88 (Rhodia Inc.), sodium chloride, sodium sulfate, polyvinyl alcohol, and ethyl alcohol; pH adjusting agents such as citric acid, succinic acid, phosphoric acid, sodium hydroxide, sodium carbonate; perfumes; dyes; and sequestering agents such as disodium ethylenediamine tetra-acetate. Such agents generally are used individually at levels of from about 0.01% to about 10%, preferably from 0.5% to about 5.0% by weight of the composition.

Shampoos may also include antidandruff agents such as pyrithione salts, preferably zinc pyrithione, as disclosed by PCT application number PCT/US98/04139, filed Mar. 4, 1998 and published as WO 98/41505, incorporated herein by reference in its entirety.

Hair Removal Personal Care Products

The organophosphorus material containing compositions of the present invention may also be employed with foam foaming shaving gels and shaving creams. Typical foaming shaving gels are disclosed by U.S. Pat. Nos. 5,902,778 to Hartmann, et al; 5,858,343 to Szymczak; and 5,853,710 to Dehan, et al, all of which are incorporated herein by reference in their entirety. Typical foam shaving creams are disclosed by U.S. Pat. Nos. 5,686,024 to Dahanayake, et al; 5,415,860 to Beucherie, et al; 5,902,574 to Stoner, et al; and 5,104,643 to Grollier, et al, all of which are incorporated herein by reference in their entirety.

The present organophosphorus material is also useful in a depilatory. An example of a depilatory is disclosed in U.S. Pat. No. 4,734,099 to Cyprien incorporated herein by reference in its entirety.

Makeup Remover

The organophosphorus material of the present invention may also be included in a makeup remover. Typical makeup removers are described by U.S. Pat. No. 5,607,680 incorporated herein by reference in its entirety. More particularly, according to the present invention, the subject compositions permit the skin and/or the eyes to be cleansed, and/or makeup to be removed efficaciously therefrom, without any attendant irritation or any discomfort whatever to the user.

Such compositions of this invention present the advantage of effecting removal of makeup in the absence of an obligatory rinsing step; this is especially advantageous in the event of application to a skin having certain skin disorders or conditions, or in the case of application to the skin under conditions not conducive to rinsing with water, such as when traveling.

Another advantage presented by the compositions according to the invention is that they are well suited for the removal of any type of makeup product, including waterproof makeup products for the eyes or makeup products having fat-rich textures, such as foundations, powders and lipsticks that are particularly suited for making-up actors.

Another notable advantage presented by the compositions according to the invention is the fact that said compositions may be employed in hot countries where the use of excessively fat-rich makeup removers gives the sensation of weight or heaviness on the skin which is often difficult to bear.

This type of formulation is advantageously formulated into the subject compositions in an amount ranging from 0.5% to 5% by weight, and preferably in an amount ranging from 1% to 2% by weight, relative to the total weight of the composition.

The diesters advantageously used for the preparation of the compositions according to the invention are those obtained by reacting a saturated or unsaturated fatty acid having from 16 to 22 carbon atoms with a polyethylene glycol in which the number of the oxyethylene recurring structural units ranges from 150 to 175.

Even more preferably, the diesters formulated into the subject compositions are selected from among polyethylene glycol distearates, polyethylene glycol dipalmitates, polyethylene glycol dioleates and polyethylene glycol dibehenates.

The diester comprising the subject compositions is advantageously present in an amount generally ranging from 1% to 5% by weight, and preferably in an amount ranging from 1% to 2% by weight, relative to the total weight of the composition.

The compositions according to the invention comprise, in addition, at least one fat constituting the fatty phase, and which is preferably selected from among fatty alcohols and oils having a melting point above 30° C.

Even more preferably, fatty alcohols are employed selected from among cetyl alcohol, stearyl alcohol and a mixture thereof. Among the oils having a melting point above 30° C., shea butter, illipe butter and cocoa butter are particularly representative.

In another especially preferred embodiment of the present invention, the aqueous phase comprising the compositions according to the invention represents at least 90% by weight, preferably at least 95% by weight and, even more preferably, at least 97% by weight of the total weight of the composition.

This aqueous phase of the compositions according to the invention preferably comprises water, in which at least one organophosphorus compound of the invention is present.

The subject composition can optionally comprise, in addition, at least one perfume, and at least one preservative, in an amount ranging from 0.1% to 1% by weight relative to the total weight of the composition.

The compositions according to this invention may be formulated as an emulsion (water-in-oil, oil-in-water), a dispersion, a gel, a cream, a lotion or a foam, or any other form typically employed in the cosmetics art.

The present invention also features a technique for removing makeup from the skin, which comprises applying a composition as described above to skin and/or to eyes which have been made up. As indicated above, the application of this composition to the skin does not result in the generation of foam.

This technique optionally includes a rinsing step, which is not mandatory.

Hand Soap

The organophosphorus material of the present invention may also be included in a hand soap. Typical hand soaps are described by U.S. Patent Application Publication No. 2006/0135384 incorporated herein by reference in its entirety. Such a soap composition includes (a) water; (b) a primary hand soap composition; (c) a biocide; and (d) the organophosphorus material of the invention as a surfactant, such that a relative contact angle value with water of at least about +100 with respect to the primary hand soap composition.

"Primary hand soap composition" refers to the collective ingredients of a soap composition of the invention exclusive of the surfactant component; optionally including a biocide. The primary soap formulation may be referred to on either a wet or dry basis. The primary hand soap composition typically includes one or more surfactants as the primary surfactants of the composition as well as preservatives, fragrances and so forth. The primary hand soap composition may contain anionic surfactants, cationic surfactants, nonionic surfactants and so forth. Examples of suitable conventional anionic surfactants generally include, but are not necessarily limited to, fatty acid soaps as well as sulfates, carboyxlates, sulfonates, sulfosuccinates, phosphonates, phosphates, sarcosinates and isethionates of hydrophobic moieties. Other suitable surfactants for the primary hand soap composition are surfactants selected from the group consisting of amine oxides, phospholipids, partially neutralized carboxylic acids and diacids, betaines, ethoxylated methylglucosides and mixtures thereof. The amount of primary surfactant(s) to be added to the composition of the present invention is somewhat dependent upon the number of primary surfactants added. However, the amount of all of the primary surfactants together generally will not exceed more than about 20-25% by weight of the composition including water.

"Primary surfactant" means a surfactant included in the primary hand soap composition.

The composition may also include other additives such as thickeners, emollients, chelating and sequestering agents, fragrances, coloring agents, opacifying agents, pearlizing agents, vitamins and the like. For example, the composition may include a polymer viscosifier or thickener such as hydroxyethyl cellulose to make the composition more aesthetically pleasing. Examples of other suitable polymer viscosifiers include, but are not necessarily limited to, hydroxypropyl cellulose, methylcellulose, and carboxymethyl cellulose. Examples of suitable chelating agents for the present invention are ethylenediaminetetra-acetic acid (EDTA), and its salts such as tetra sodium EDTA. An example of a particular pearlizing agent is ethylene glycol distearate. Generally, these additives are used in amounts, which do not affect the essential nature of the composition with respect to its antimicrobial properties.

EXAMPLE 1

Egg Shell Tests

In this example egg-shell was stained with green/black tea stain.

FIG. 1 shows a photograph of egg-shell brushed with commercial toothpaste, then stained with green (left) and black (right) tea, and then brushed again with commercial toothpaste. This resulted in no removal of tea stain.

Figure 2:
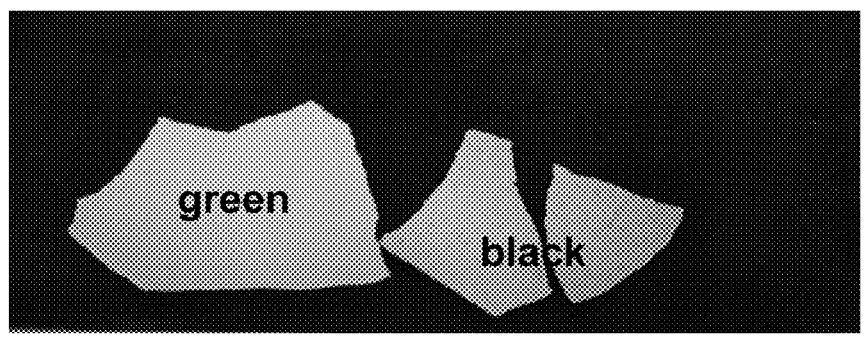
FIG. 2 shows a photograph of egg-shell brushed with commercial toothpaste plus 20% PEG400 phosphate ester (polyethylene glycol 400 phosphate ester), then stained with green (left) and black (right) tea, and then brushed again with toothpaste plus 20% PEG400 phosphate ester.

In another experiment PEG400 phosphate ester (a polyethylene glycol phosphate ester) was mixed directly into the toothpaste without neutralization. Egg-shell was brushed with commercial toothpaste plus 20% PEG400 phosphate ester, then stained with green and black tea, and then brushed again with commercial tooth-paste plus 20% PEG400 phosphate ester. FIG. 2 shows a photograph of the egg-shell brushed with the commercial toothpaste plus 20% PEG400 phosphate ester, then stained with green (left) and black (right) tea, and then brushed again with commercial toothpaste plus 20% PEG400 phosphate ester. This resulted in good removal of tea stain.

Figure 3:
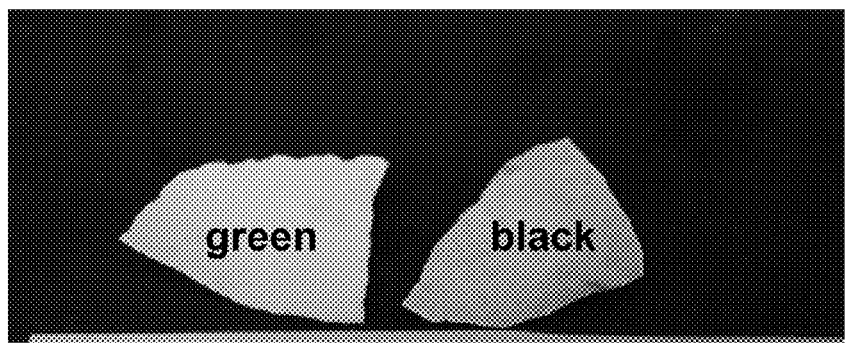
FIG. 3 shows a photograph of egg-shell brushed with commercial toothpaste plus 20% SDS, then stained with green (left) and black (right) tea, and then brushed with commercial toothpaste plus 20% SDS.

In another experiment 20% sodium dodecyl sulphate (SDS) was mixed into the commercial toothpaste. The 20% SDS was used as a 100% powder. FIG. 3 shows a photograph of egg-shell brushed with the commercial toothpaste plus 20% SDS, then stained with green (left) and black (right) tea, and then brushed with commercial toothpaste plus 20% SDS. This resulted in no/slight removal of tea stain.

Figure 4:
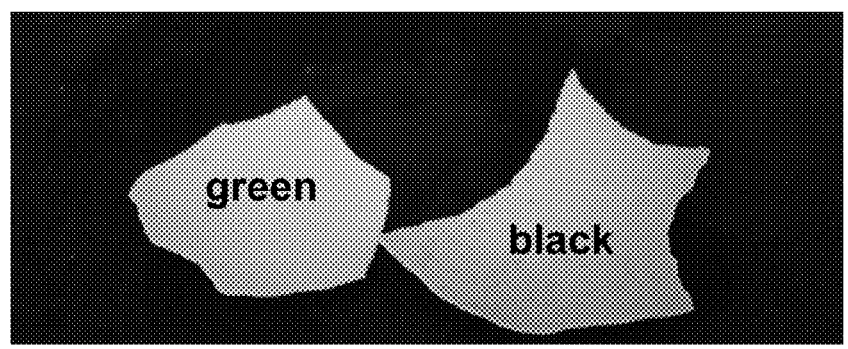
FIG. 4 shows a photograph of egg-shell brushed with commercial toothpaste plus 20% PEG1000 phosphate ester, then stained with green (left) and black (right) tea, and then brushed again with commercial toothpaste plus 20% P1000 phosphate ester.

In another experiment PEG1000 phosphate ester (a polyethylene glycol phosphate ester) was mixed directly into the toothpaste without neutralization. FIG. 4 shows a photograph of egg-shell brushed with commercial toothpaste plus 20% PEG1000 phosphate ester (a polyethylene glycol phosphate ester), then stained with green (left) and black (right) tea, and then brushed again with commercial toothpaste plus 20% PEG1000 phosphate ester. This resulted in good removal of tea stain.

In a separate test it was noted that treatment of egg-shell with SDS or PEG phosphate ester, then staining and then simple rinsing does not improve removal of stain compared to untreated egg-shell. This implies improved cleaning is not due to creation of anti-soiling layer, but due to better cleaning capability.

EXAMPLES F1-F20 AND COMPARATIVE EXAMPLE F-C1

Some organophosphorus materials were tested on fabric to study their surface effects. The treated fabric substrates of Examples F1 to F5 were made as follows.

Phosphate esters P1-P5 according to the above described structure (IX):

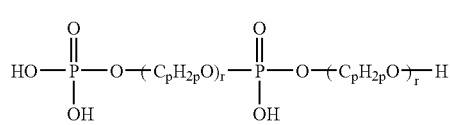

wherein p and r are in each case as set forth in TABLE I below were used to make treatment compositions T1-T15.

TABLE I

| Phosphate Esters according to Structure (IX) | | |
|---|---|---|
| Phosphate ester # | p | r |
| P1 | 2 | 4.5 |
| P2 | 2 | 9 |
| P3 | 2 | 13.5 |
| P4 | 2 | 22.5 |
| P5 | 3 | 7.3 |

Treatment compositions T1-T15 were each aqueous solutions comprising water, a respective one of the phosphate esters P1-P5, and in some case, other components. The amounts of phosphate esters P1-P5, the identity of any other components, and the amounts of such phosphate esters and other components contained in each of the treatment compositions are summarized in TABLE II below. Treatment compositions T16, T17, T18, T19, and T20 were each aqueous solutions comprising water contained poly(vinyl alcohol) polymer, but did not contain any organophosphorus compound. The respective poly(vinyl alcohol) polymers used are identified in the footnotes to TABLE II below.

TABLE II

| | Treatment Compositions | | | |
|---|---|---|---|---|
| Treatment | Phosphate Ester | | Other Components | |
| Composition #[1] | # | Amount (wt %) | Component | Amount |
| T1 | P1 | 1 | — | — |
| T2 | P2 | 0.1 | — | — |
| T3 | P2 | 1 | — | — |
| T4 | P2 | 5 | — | — |
| T5 | P3 | 1 | — | — |
| T6 | P3 | 5 | — | — |
| T7 | P4 | 1 | — | — |
| T8 | P2 | 5 | Ca(OH)$_2$ | to pH 5.21 |
| T9 | P2 | 5 | AlCl$_3$•7H$_2$O | 0.1 wt % |
| T10 | P2 | 5 | Ludox particles[2] | 5 wt % |
| T11 | P3 | 0.3 | pvOH[3] | 0.2 wt % |
| T12 | P3 | 0.5 | pvOH[3] | 0.1 wt % |
| T13 | P3 | 1 | pvOH[3] | 0.1 wt % |
| T14 | P5 | 1 | — | — |
| T15 | P5 | 5 | — | — |
| T-16 | — | — | pvOH[3] | 0.1 wt % |
| T-17 | — | — | pvOH[4] | 0.1 wt % |
| T-18 | — | — | pvOH[4] | 1.0 wt % |
| T-19 | — | — | pvOH[5] | 0.1 wt % |
| T-20 | — | — | pvOH[5] | 1.0 wt % |

[1]in each case, solution was neutralized with NaOH to a PH value of 7
[2]aluminum coated silica nanoparticles specific surface area 230 m$^2$/g, (Ludox CL particles, WR Grace)
[3]Poly(vinyl alcohol) having a molecular weight of about 150,000 g/mol and a degree of hydrolysis equal to about 88%, (Erkol ™ poly(vinyl alcohol), Rhodia Inc.)
[4]Poly(vinyl alcohol) having a molecular weight of about 31,000 to about 50,000 g/mol and a degree of hydrolysis equal to about 98%, (#363138, Aldrich)
[5]Poly(vinyl alcohol) having a molecular weight of about 146,000 to about 186,000 g/mol and a degree of hydrolysis equal to about 98%, (#363162, Aldrich)

Nonwoven poly(propylene) fabric was used to show the feasibility of the effect of the previously described samples on low energy surfaces. The nonwoven poly(propylene) fabric samples (each 30 cm×20 cm, having a weight about 17 grams per square meter of fabric and an average thickness of about 0.12 millimeters ("mm")) were cut, marked to distinguish upper side to be treated, weighed, and placed against an aluminum foil. Gloves were worn during all handling of the fabric. The fabric samples of F1-F20 were each treated with a respective one of the treatment compositions T1 to T20 by dipping the fabric sample into the composition, removing the fabric sample from the composition and then squeezing excess composition out of the fabric. The fabric samples of Comparative Example F-C1 remained untreated. The dampened fabrics were then dried at 60° C. for 1 hour in an oven, and cooled to room temperature. The difference between the weight of the fabric after treatment and the weight of the fabric before treatment was typically from about 5 to about 30 wt %, corresponding to about 0.85-5 grams phosphate ester per square meter ("m$^2$") of treated fabric.

The treated fabric samples were evaluated by rinsing in water and measuring the surface tension of rinse water according to ASTM 1331 (except as specifically noted below). In each case, A 20×18 cm sample (360 cm$^2$ total area) was cut from the treated fabric. The fabric sample was placed onto 40 milliliters ("mL") of a 0.909 wt % NaCl aqueous solution and the fabric was stirred in the solution for 10 seconds, the fabric was then allowed to sit without any agitation for 5 minutes, was then stirred for 10 seconds, and was then removed from the solution. The solution was allowed to rest for 10 minutes and the surface tension of the solution was then determined using a Wilhemy plate (Kruss Instruments). The surface tension results are set forth in TABLE II below in milliNewtons per meter (mN/m) for each of the treated fabrics of Examples F1 to F20 and Comparative Example F-C1.

The surface tension of a control aqueous solution of 0.909 wt % NaCl was determined to be about 72 mM/m. A reduction in the surface tension of the surface tension of the solution used to rinse a treated fabric sample provides a rough indication of the amount of phosphorous compound washed off of the fabric samples of Examples F1 to F20 as compared to Comparative Example F-C1 by the rinse procedure. A rinse solution surface tension that is close to that of the control salt solution indicates minimal rinse-off, and increasing magnitude of the difference between the rinse solution and the control salt solution indicating increasing amount of phosphorous compound rinse-off.

Samples of the treated fabrics of Examples F1 to F20 and Comparative Example F-C1 were also evaluated by a "strikethrough" test according to EDANA test 150.3-96 (except as specifically noted below). In each case, a 12×12 cm sample of treated fabric was placed on top of a stack of 10 filter papers (ERT-FF3) and placed under a 50 mL separating funnel. A conductivity electrode made from stainless steel was placed on top of the stack of filter papers and under the treated fabric. A burette was filled with 0.909 wt % NaCl (saline solution) up to 50 mL. Making sure that the funnel stopcock was closed, a 5 mL aliquot of the saline solution was delivered from the burette to the funnel. The funnel stopcock was opened and the time from the moment the liquid touched the fabric until all liquid disappears into the stack of filter papers (the "strikethrough time") was measured. After 60 seconds, a second 5 mL aliquot of the saline solution was introduced to the fabric sample. Three samples were tested for each treated fabric and five "gushes", that is separate 5 mL aliquots of salt solution, were used for each sample of treated fabric. The results for treated fabrics of Examples F1 to F20 and Comparative Example F-C1 are set forth in TABLE III below in seconds (s) as the arithmetic average of the results for three samples of each treated fabrics of Examples F1-F20 and Comparative Example F-C1.

TABLE III

Treated Fabric Rinse and Strikethrough Results

| Treated Fabric EX # | Treatment Composition # | Rinse Surface Tension (mN/m) | Strikethrough Gush # | Average Strikethrough Time (s) |
|---|---|---|---|---|
| F1 | T1 | 55.4 | 1 | 17.35 |
|  |  |  | 2 | 18.73 |
|  |  |  | 3 | 18.21 |
|  |  |  | 4 | 14.5 |
|  |  |  | 5 | 13.49 |
| F2 | T2 | 55.0 | 1 | >60 |
|  |  |  | 2 | >60 |
|  |  |  | 3 | >60 |
|  |  |  | 4 | >60 |
|  |  |  | 5 | >60 |
| F3 | T3 | 52.5 | 1 | 4.77 |
|  |  |  | 2 | 17.9 |
|  |  |  | 3 | 18.1 |
|  |  |  | 4 | 16.01 |
|  |  |  | 5 | 13.92 |
| F4 | T4 | 50.1 | 1 | 3.39 |
|  |  |  | 2 | 10.11 |
|  |  |  | 3 | 10.37 |
|  |  |  | 4 | 8.52 |
|  |  |  | 5 | 7.46 |
| F5 | T5 | 48.6 | 1 | 2.70 |
|  |  |  | 2 | 5.13 |
|  |  |  | 3 | 5.62 |
|  |  |  | 4 | 5.21 |
|  |  |  | 5 | 5.50 |
| F6 | T6 | 48.3 | 1 | 2.94 |
|  |  |  | 2 | 5.12 |
|  |  |  | 3 | 5.92 |
|  |  |  | 4 | 5.01 |
|  |  |  | 5 | 5.94 |
| F7 | T7 | 51.0 | 1 | 11.36 |
|  |  |  | 2 | 23.04 |
|  |  |  | 3 | 34.64 |
|  |  |  | 4 | >60 |
|  |  |  | 5 | >60 |
| F8 | T8 | 53.0 | 1 | 2.15 |
|  |  |  | 2 | 4.78 |
|  |  |  | 3 | 6.2 |
|  |  |  | 4 | 4.93 |
|  |  |  | 5 | 4.4 |
| F9 | T9 | 50.9 | 1 | 3.52 |
|  |  |  | 2 | 4.67 |
|  |  |  | 3 | 5.1 |
|  |  |  | 4 | 5.4 |
|  |  |  | 5 | 4.5 |
| F10 | T10 | 50.2 | 1 | 2.97 |
|  |  |  | 2 | 2.72 |
|  |  |  | 3 | 3.51 |
|  |  |  | 4 | 5.17 |
|  |  |  | 5 | 4.77 |
| F11 | T11 | 53.1 | 1 | 2.890 |
|  |  |  | 2 | 3.660 |
|  |  |  | 3 | 4 |
|  |  |  | 4 | 3.8 |
|  |  |  | 5 | 3.94 |
| F12 | T12 | 48.3 | 1 | 3.17 |
|  |  |  | 2 | 3.96 |
|  |  |  | 3 | 4.09 |
|  |  |  | 4 | 4.74 |
|  |  |  | 5 | 3.95 |
| F13 | T13 | 52.5 | 1 | 2 |
|  |  |  | 2 | 3.18 |
|  |  |  | 3 | 3.14 |
|  |  |  | 4 | 3.23 |
|  |  |  | 5 | 3.49 |
| F14 | T14 | 48.6 | 1 | 3.14 |
|  |  |  | 2 | 11.48 |
|  |  |  | 3 | 25.49 |
|  |  |  | 4 | 21.01 |
|  |  |  | 5 | 9.82 |

TABLE III-continued

Treated Fabric Rinse and Strikethrough Results

| Treated Fabric EX # | Treatment Composition # | Rinse Surface Tension (mN/m) | Strikethrough Gush # | Average Strikethrough Time (s) |
|---|---|---|---|---|
| F15 | T15 | 45.8 | 1 | 2.55 |
| | | | 2 | 12.15 |
| | | | 3 | 31.82 |
| | | | 4 | 29.41 |
| | | | 5 | 19.02 |
| F16 | T16 | 45.4 | 1 | 5.79 |
| | | | 2 | 4.9 |
| | | | 3 | 5.01 |
| | | | 4 | 5.75 |
| | | | 5 | 5.59 |
| F17 | T17 | 51.06 | 1 | 3.33 |
| | | | 2 | 4.22 |
| | | | 3 | 3.66 |
| | | | 4 | 3.24 |
| | | | 5 | 3.1 |
| F18 | T18 | 53.08 | 1 | 3.05 |
| | | | 2 | 12.14 |
| | | | 3 | 8.43 |
| | | | 4 | 6.58 |
| | | | 5 | 6.71 |
| F19 | T19 | 54.48 | 1 | 1.93 |
| | | | 2 | 3.16 |
| | | | 3 | 3.16 |
| | | | 4 | 3.2 |
| | | | 5 | 3.18 |
| F20 | T20 | 50.16 | 1 | 2.73 |
| | | | 2 | 3.2 |
| | | | 3 | 3.15 |
| | | | 4 | 2.79 |
| | | | 5 | 3 |
| F-C1 | not treated | 66 | 1 | >360 |
| | | | 2 | >360 |
| | | | 3 | >360 |
| | | | 4 | >360 |
| | | | 5 | >360 |

It is apparent that embodiments other than those expressly described above come within the spirit and scope of the present claims. Thus, the present invention is not defined by the above description, but rather is defined by the claims appended hereto.

The invention claimed is:

1. A personal care composition, comprising:
(a) a surface active agent,
(b) a hydrophilizing agent comprising a compound selected from the group consisting of:
(b)(1) organophosphorus compounds according to structure (I):

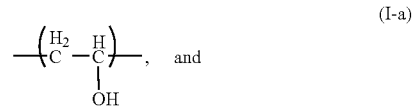

wherein:
each $R^1$ and $R^2$ are independently absent or O, provided that at least one of $R^1$ and $R^2$ is O, each $R^3$ is independently an alkyleneoxy, or poly(alkyleneoxy) group, which may optionally be substituted on one or more carbon atoms of such alkyleneoxy, or poly(alkyleneoxy) group, by hydroxyl, alkyl, hydroxyalkyl, alkoxy, alkenyl, aryl, or aryloxy groups, $R^5$ and $R^4$ are each independently absent or an alkyleneoxy, or poly(alkyleneoxy) group, which may optionally be substituted on one or more carbon atoms of such alkyleneoxy, or poly(alkyleneoxy) group, by hydroxyl, alkyl, hydroxyalkyl, alkoxy, alkenyl, aryl, or aryloxy groups, $R^6$, $R^8$ and $R^7$ are each independently H, or $(C_1\text{-}C_{30})$ hydrocarbon, which hydrocarbon may optionally be substituted on one or more carbon atoms by hydroxyl, fluorine, alkyl, alkenyl or aryl and/or interrupted at one or more sites by an O, N, or S heteroatom, or $—POR^9R^{10}$, $R^9$ and $R^{10}$ are each independently hydroxyl, alkoxy, aryloxy, or $(C_1\text{-}C_{30})$hydrocarbon, which hydrocarbon may optionally be substituted on one or more carbon atoms by hydroxyl, fluorine, alkyl, alkenyl or aryl and/or interrupted at one or more sites by an O, N, or S heteroatom, and m is an integer of from 1 to 5, (b)(2) salts of organophosphorus compounds according to structure (I),
(b)(3) condensation reaction products of two or more molecules of one or more organophosphorus compounds according to structure (I), and
(b)(4) mixtures comprising two or more of the compounds, salts, and/or reaction products of (b)(1), (b)(2), and (b)(3), and
(c) a vinyl alcohol material selected from the group consisting of:
(c)(1) polymers comprising monomeric units according to structure (I-a):

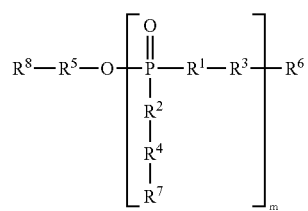

(c)(2) salts of polymers (c)(1),
(c)(3) reaction products of two or more molecules of one or more polymers (c)(1);
wherein the vinyl alcohol material has a weight average molecular weight of about 50,000 to 200,000, and a degree of hydrolysis of at least 88%; and
the composition comprises about 0.01 to 20 parts by weight of the vinyl alcohol material per 100 parts by weight of the composition.

2. The personal care composition of claim 1, further comprising at least one member selected from the group consisting of a pearlizing agent, a silicone hair conditioning agent, and an antidandruff ingredient.

3. The personal care composition of claim 2, wherein said composition further comprises:
a) a pearlizing agent
b) a nonionic surfactant
c) an amphoteric surfactant
d) a glycol emulsifier
e) water.

4. The personal care composition of claim 1, further comprising one or more components selected from the group consisting of pearlescent additives, an amphoteric surfactant, a glycol emulsifier, and water.

5. The personal care composition of claim 4, further comprising a silicone compound.

6. The personal care composition of claim 1, wherein the organophosphorus material is present in a liquid carrier.

7. The personal care composition of claim 1, wherein the composition is for cleaning hair or skin and comprises:
    the organophosphorus material,
    at least one detersive surfactant, and further comprises;
    at least one member selected from the group consisting of a pearlizing agent, a silicone hair conditioning agent, and an antidandruff ingredient, provided that a 10% aqueous solution of said composition has a pH from about 4 to about 12.

8. The personal care composition of claim 7, wherein the silicone compound is an alpha, omega-trimethylsilyl-polydimethylsiloxane having a viscosity at 25° C. of at least 25 centistokes and less than 60,000 centistokes.

9. A method for cleaning hair or skin comprising applying an effective amount of the personal care composition of claim 1, provided that a 10% aqueous solution of said composition has a pH from about 4 to about 9.

10. The method of claim 9, wherein the composition further comprises at least one member selected from the group consisting of a pearlizing agent, a silicone hair conditioning agent, and an antidandruff ingredient.

11. The method of claim 10, wherein the composition further comprises:
    a) a pearlizing agent
    b) a nonionic surfactant
    c) an amphoteric surfactant
    d) a glycol emulsifier
    e) water.

12. The method of claim 10, wherein said composition further comprises at least one amphoteric surfactant and said amphoteric surfactant is at least one member selected from the group consisting of:
    the alkali salts of alkyl amphodipropionates, alkyl amphodiacetates, alkyl amphoglycinates, alkyl amphopropyl sulfonates and alkyl amphopropionates wherein alkyl represents an alkyl group having 6 to 20 carbon atoms.

13. The method of claim 12, wherein in said at least one amphoteric surfactant, the alkyl group is derived from coconut oil or is a lauryl group.

14. A method for cleaning hair or skin comprising applying an effective amount of the personal care composition of claim 1 to hair or skin in need of cleaning.

15. A method for treating a human body comprising applying an effective amount of the personal care composition of claim 1 to a human body in need of treatment.

16. A cosmetic composition for removing makeup from the skin and/or eyes, and/or for the cleansing thereof, comprising:
    (a) a cosmetically acceptable vehicle or carrier comprising a fatty phase and an aqueous phase,
    (b) a hydrophilizing agent comprising a compound selected from the group consisting of:
    (b)(1) organophosphorous compounds according to structure (I):

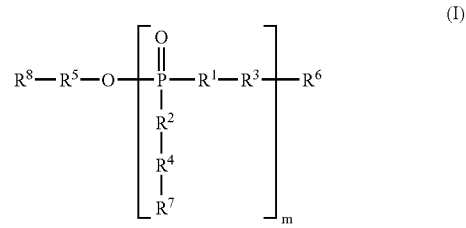

wherein:
    each $R^1$ and $R^2$ are each independently absent or O, provided that at least one of $R^1$ and $R^2$ is O,
    each $R^3$ is independently an alkyleneoxy, or poly(alkyleneoxy) group, which may optionally be substituted on one or more carbon atoms of such alkyleneoxy, or poly(alkyleneoxy) group, by a hydroxyl, alkyl, hydroxyalkyl, alkoxy, alkenyl, aryl, or aryloxy group,
    $R^5$ and $R^4$ are each independently absent or an alkyleneoxy, or poly(alkyleneoxy) group, which may optionally be substituted on one or more carbon atoms of such alkyleneoxy, or poly(alkyleneoxy) group, by a hydroxyl, alkyl, hydroxyalkyl, alkoxy, alkenyl, aryl, or aryloxy group,
    $R^6$, $R^8$, and $R^7$ are each independently H, or ($C_1$-$C_{30}$) hydrocarbon, which hydrocarbon may optionally be substituted on one or more carbon atoms by hydroxyl, fluorine, alkyl, alkenyl or aryl and/or interrupted at one or more sites by an O, N, or S heteroatom, or —$POR^9R^{10}$,
    $R^9$ and $R^{10}$ are each independently hydroxyl, alkoxy, aryloxy, or ($C_1$-$C_{30}$)hydrocarbon, which hydrocarbon may optionally be substituted on one or more carbon atoms by hydroxyl, fluorine, alkyl, alkenyl or aryl and/or interrupted at one or more sites by an O, N, or S heteroatom, and
    m is an integer of from 1 to 5,
    (b)(2) salts of organophosphorus compounds according to structure (I),
    (b)(3) condensation reaction products of two or more molecules of one or more organophosphorus compounds according to structure (I), and
    (b)(4) mixtures comprising two or more of the compounds, salts, and/or reaction products of (b)(1), (b)(2), and (b)(3), and
    (c) a vinyl alcohol material selected from the group consisting of:
    (c)(1) polymers comprising monomeric units according to structure (I-a):

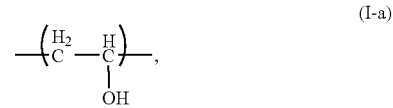

(c)(2) salts of polymers (c)(1), and
    (c)(3) reaction products of two or more molecules of one or more polymers (c)(1);
    wherein the vinyl alcohol material has a weight average molecular weight of about 50,000 to 200,000, and a degree of hydrolysis of at least 88%; and the composition comprises about 0.01 to 20 parts by weight of the vinyl alcohol material per 100 parts by weight of the composition; and (d) a polyethylene glycol diester.

17. The makeup remover/skin cleanser cosmetic composition of claim 16, wherein the cosmetically acceptable vehicle comprises the fatty phase and the aqueous phase, and
comprising from 1% to 5% by weight of (d) the polyethylene glycol diester selected from the group consisting of a polyethylene glycol distearate, polyethylene glycol dipalmitate, polyethylene glycol dioleate and polyethylene glycol dibehenate and from 0.5% to 5% by weight of the organophosphorus material.

18. The makeup remover/skin cleanser composition as defined by claim 16, comprising from 1% to 2% by weight of said polyethylene glycol diester (d) relative to the total weight of the composition.

19. The makeup remover/skin cleanser composition as defined by claim 16, said aqueous phase comprising at least 90% by weight thereof.

20. The makeup remover/skin cleanser composition as defined by claim 16, said aqueous phase comprising at least 95% by weight thereof.

21. The makeup remover/skin cleanser composition as defined by claim 16, wherein the composition is in the form of an emulsion, gel, cream, lotion, or foam.

22. The makeup remover/skin cleanser composition as defined by claim 16, further comprising at least one perfume.

23. A method for the removal of makeup from skin and/or eyes to which makeup has been applied, comprising applying thereto an effective amount of the makeup remover/skin cleanser composition as defined by claim 16.

24. A method for cleansing skin and/or eyes in need of such treatment, comprising applying thereto an effective amount of the makeup remover/skin cleanser composition as defined by claim 16.

* * * * *